United States Patent
Roe et al.

(10) Patent No.: US 6,703,536 B2
(45) Date of Patent: Mar. 9, 2004

(54) DISPOSABLE ABSORBENT ARTICLE HAVING A SKIN CARE COMPOSITION CONTAINING AN ENZYME INHIBITOR

(75) Inventors: Donald Carroll Roe, West Chester, OH (US); Francis James Rourke, Sharonville, OH (US); Scott Edward Osborne, Middletown, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 10/323,386

(22) Filed: Dec. 18, 2002

(65) Prior Publication Data

US 2003/0139711 A1 Jul. 24, 2003

Related U.S. Application Data

(63) Continuation-in-part of application No. 09/623,813, filed as application No. PCT/US99/05311 on Mar. 11, 1999, now abandoned, which is a continuation-in-part of application No. 09/041,266, filed on Mar. 12, 1998, now abandoned.

(51) Int. Cl.[7] .................................................. A61F 13/15
(52) U.S. Cl. ..................... 604/360; 604/367; 604/359
(58) Field of Search ................................. 604/364, 367, 604/360, 359, 384; 424/76.1–76.4; 524/99

(56) References Cited

U.S. PATENT DOCUMENTS

| | | | |
|---|---|---|---|
| 2,804,424 A | 8/1957 | Stirn et al. | |
| 2,883,366 A | 4/1959 | Glusenkamp | |
| 3,208,984 A | 9/1965 | Dekking | |

(List continued on next page.)

FOREIGN PATENT DOCUMENTS

| | | |
|---|---|---|
| CA | 2019557 AA | 12/1990 |
| DE | 4136540 A1 | 5/1992 |
| EP | 0 093 186 A1 | 11/1983 |

(List continued on next page.)

OTHER PUBLICATIONS

Uldall, Chr., "Comparative Studies on Feces of Healthy Breast–, Bottle– and Spoon–fed Infants", Report from the Laboratory of the Copenhangen Board of Health, Acta. Paediatr., vol. 29, pp. 339–366 (1942).

White, C.M., "Cholestyramine Ointment to Treat Buttocks Rash and Anal Excoriation in an Infant", Ann Pharmacother, vol. 30, pp. 954–956 (Sep. 1996).

*Primary Examiner*—Weilun Lo
*Assistant Examiner*—Jacqualine F Stephens
(74) *Attorney, Agent, or Firm*—Caroline H. Wei Berk; Ken K. Patel; Steven W. Miller

(57) ABSTRACT

An absorbent article, at least a portion of which comprises a skin care composition that comprises an enzyme inhibitor and is at least partially transferred from the article to the skin of a wearer of the article as a result of normal contact, wearer motion and/or body heat. The enzyme inhibitor is transferred to the skin with the skin care composition and is available at the skin/urine and skin/feces interfaces to inhibit enzymatic activity on the skin and to reduce or prevent the occurrence of inflammation. Repeated application of similar treated articles to the wearer's skin provides an available source with which the enzyme inhibitor transfers onto the skin continuously over time and accumulates to provide a pro-active defense against harmful enzymes for the treatment and/or prevention of diaper dermatitis.

24 Claims, 2 Drawing Sheets

U.S. PATENT DOCUMENTS

| | | |
|---|---|---|
| 3,489,148 A | 1/1970 | Duncan et al. |
| 3,490,454 A | 1/1970 | Goldfarb et al. |
| 3,585,998 A | 6/1971 | Hayford et al. |
| 3,707,148 A | 12/1972 | Bryce |
| 3,875,942 A | 4/1975 | Roberts et al. |
| 3,896,807 A | 7/1975 | Buchalter |
| 3,902,493 A | 9/1975 | Baier et al. |
| 3,920,015 A | 11/1975 | Wortham |
| 3,935,862 A | 2/1976 | Kraskin |
| 3,957,971 A | 5/1976 | Oleniacz |
| 3,964,486 A | 6/1976 | Blaney |
| 4,034,077 A | 7/1977 | Hill et al. |
| 4,112,167 A | 9/1978 | Dake et al. |
| 4,263,363 A | 4/1981 | Buck et al. |
| 4,273,786 A | 6/1981 | Kraskin |
| 4,324,247 A | 4/1982 | Aziz |
| 4,401,712 A | 8/1983 | Morrison |
| 4,450,151 A | 5/1984 | Shinozawa |
| 4,478,853 A | 10/1984 | Chaussee |
| 4,513,051 A | 4/1985 | Lavash |
| 4,556,560 A | 12/1985 | Buckingham |
| 4,565,727 A | 1/1986 | Giglia et al. |
| 4,569,343 A | 2/1986 | Kimura et al. |
| 4,576,817 A | 3/1986 | Montgomery et al. |
| 4,623,339 A | 11/1986 | Ciraldo et al. |
| 4,657,537 A | 4/1987 | Zimmerer |
| 4,666,765 A | 5/1987 | Caldwell et al. |
| 4,685,909 A | 8/1987 | Berg et al. |
| 4,690,821 A | 9/1987 | Smith et al. |
| 4,704,112 A | 11/1987 | Suzuki et al. |
| 4,707,293 A | 11/1987 | Ferro |
| 4,753,643 A | 6/1988 | Kassai |
| 4,790,836 A | 12/1988 | Brecher |
| 4,806,478 A | 2/1989 | Stahl |
| 4,842,593 A | 6/1989 | Jordan et al. |
| 4,861,584 A | 8/1989 | Powell, Jr. et al. |
| 4,882,204 A | 11/1989 | Tenenbaum |
| 4,900,317 A | 2/1990 | Buell |
| 4,904,524 A | 2/1990 | Yoh |
| 4,929,498 A | 5/1990 | Suskind et al. |
| 4,959,059 A | 9/1990 | Eilender et al. |
| 4,970,220 A | 11/1990 | Chaussee |
| 4,990,144 A | 2/1991 | Blott |
| 4,996,238 A | 2/1991 | Matravers |
| 5,091,193 A | 2/1992 | Enjoiras et al. |
| 5,110,593 A | 5/1992 | Benford |
| 5,192,277 A | 3/1993 | Chung et al. |
| 5,194,261 A | 3/1993 | Pichierri |
| 5,264,460 A | 11/1993 | Jakobson et al. |
| 5,321,098 A | 6/1994 | Lal |
| 5,362,488 A | 11/1994 | Sibley et al. |
| 5,370,132 A | 12/1994 | Weber et al. |
| 5,376,655 A | 12/1994 | Imaki et al. |
| 5,409,903 A | 4/1995 | Polak et al. |
| 5,415,649 A | 5/1995 | Watanabe et al. |
| 5,417,981 A | 5/1995 | Endo et al. |
| 5,436,007 A | 7/1995 | Hartung et al. |
| 5,466,396 A | 11/1995 | Madison et al. |
| 5,509,915 A | 4/1996 | Hanson et al. |
| 5,525,346 A | 6/1996 | Hartung et al. |
| 5,558,655 A | 9/1996 | Jezzi et al. |
| 5,607,760 A | 3/1997 | Roe |
| 5,609,587 A | 3/1997 | Roe |
| 5,612,045 A | 3/1997 | Syverson |
| 5,618,529 A | 4/1997 | Pichierri |
| 5,635,191 A | 6/1997 | Roe et al. |
| 5,643,588 A | 7/1997 | Roe et al. |
| 5,674,509 A | 10/1997 | Date et al. |
| 5,702,380 A | 12/1997 | Walker |
| 5,869,033 A | 2/1999 | Schulz |
| 5,871,763 A | 2/1999 | Luu et al. |
| 6,051,749 A | 4/2000 | Schulz |
| 6,066,673 A | 5/2000 | Mciver et al. |
| 6,107,537 A | 8/2000 | Elder et al. |

FOREIGN PATENT DOCUMENTS

| | | |
|---|---|---|
| EP | 0 297 828 A1 | 1/1989 |
| EP | 0 555 116 A2 | 8/1993 |
| EP | 0 564 307 A1 | 10/1993 |
| EP | 0 606 046 A1 | 7/1994 |
| EP | 0 631 768 A1 | 1/1995 |
| EP | 0 682 868 A1 | 11/1995 |
| EP | 0 692 263 A2 | 1/1996 |
| EP | 0 815 841 A1 | 1/1998 |
| EP | 0 875 233 A1 | 11/1998 |
| EP | 0 958 833 A1 | 11/1999 |
| FR | 2660552 A1 | 10/1991 |
| FR | 2675341 A1 | 10/1992 |
| FR | 2700698 A1 | 11/1992 |
| FR | 2680448 A1 | 2/1993 |
| FR | 2714603 | 7/1995 |
| GB | 2033751 A | 5/1980 |
| JP | 61-028078 | 2/1986 |
| JP | 2-31756 | 2/1990 |
| JP | 02-129110 A | 5/1990 |
| JP | 04-182423 | 6/1992 |
| JP | 07-118691 A | 10/1993 |
| JP | 05-285170 | 11/1993 |
| JP | 08-19595 | 1/1996 |
| JP | 08-52175 | 2/1996 |
| JP | 09-028730 | 2/1997 |
| WO | WO 92/20319 A1 | 11/1992 |
| WO | WO 93/16681 A1 | 9/1993 |
| WO | WO 97/38735 A1 | 10/1997 |
| WO | WO 98/03147 A1 | 1/1998 |
| WO | W) 98/26808 | 6/1998 |
| WO | WO 00/10497 A1 | 3/2000 |
| WO | WO 00/10500 A1 | 3/2000 |
| WO | WO 00/38625 A2 | 7/2000 |
| WO | WO 00/38626 A2 | 7/2000 |
| WO | WO 00/38747 A2 | 7/2000 |

DISPOSABLE ABSORBENT ARTICLE HAVING A SKIN CARE COMPOSITION CONTAINING AN ENZYME INHIBITOR

CROSS REFERENCE TO RELATED APPLICATIONS

This application is a continuation-in-part of U.S. application Ser. No. 09/623,813 now abandoned, filed on Sep. 8, 2000 now abandoned, which is the National Stage of International Application No. PCT/US99/05311, filed on Mar. 11, 1999, which is a continuation-in-part-of and claims the benefit of U.S. application Ser. No. 09/041,266 now abandoned, filed on Mar. 12, 1998.

BACKGROUND OF THE INVENTION

The invention relates to absorbent articles such as diapers, training pants, adult incontinence briefs, feminine hygiene products and the like, that incorporate a skin care composition that comprises an enzyme inhibitor, preferably on a wearer-contacting surface. During normal wear of the article the enzyme inhibitor is transferred with the skin care composition to at least a portion of the wearer's skin where it is available to inactivate fecal enzymes and reduce the redness and inflammation that can occur following prolonged exposure of skin to body wastes.

Diaper rash is a common form of irritation and inflammation of those parts of an infant's body normally covered by a diaper. This condition is also referred to as diaper dermatitis, napkin dermatitis, napkin rash and nappy rash. While certainly more common in infants, this condition is not, in fact, limited to infants. Any individual who suffers from incontinence to the extent that the use of absorbent articles is required may develop this condition. Susceptible individuals range from newborns, to the elderly, to critically ill or nonambulatory individuals. 21 C.F.R. 333.503 defines diaper rash as "[a]n inflammatory skin condition in the diaper area (perineum, buttocks, lower abdomen, and inner thighs) caused by one or more of the following factors: moisture, occlusion, chafing, continued contact with urine or feces or both, or mechanical or chemical irritation." It is generally accepted by the medical profession that true diaper rash or diaper dermatitis is a condition which is, in its most simple stages, a contact irritant dermatitis resulting from extended contact of the skin with urine, or feces, or both. Among the most commonly accepted factors linked to diaper rash are ammonia, fecal enzymes, bacteria, the products of bacterial action, urine pH, and *Candida albicans*.

Many types of disposable absorbent products, such as diapers, training pants, adult incontinence devices, sanitary napkins, panty liners, and the like, are available that have a high capacity for absorbing urine and other body exudates. Disposable products of this type generally comprise some sort of liquid-pervious topsheet material, an absorbent core, and a liquid-impervious backsheet material. Although these types of absorbent structures may be highly efficient for the absorption of liquids, they cannot absorb bowel movements. Typically, the bowel movement is trapped between the outer surface of the fluid-permeable topsheet and the skin of the wearer, much of it adhering to the wearer's skin. Thus the skin is exposed to contact with feces, often for long periods of time, and is susceptible to irritants present in the feces that can produce or contribute to diaper rash.

Because enzymes are widely distributed in plants, molds, bacteria, milk, milk products, and almost all animal tissues as well as in digestive juices in the gastrointestinal tract, they are almost always present in the diapered area when it has been soiled by human waste. Enzymes present in feces include proteolytic enzymes, lipases and other esterases and diesterases, ureases and other enzymes including amylases, elastases, nucleases, and the like. Although the relative contribution of the different types of enzymes to skin irritation is unknown, there is evidence that at least fecal proteolytic and lipolytic enzymes, of intestinal and/or pancreatic origin, play a direct role in causing the skin inflammation of diaper rash.

Studies with inhibitors designed to inhibit the enzymatic activity of various classes of proteases have shown that serine proteases, cysteine proteases and metalloproteases were the most likely to be responsible for the overall proteolytic activity of feces. It is known that the serine proteases trypsin and chymotrypsin, in particular, are nearly always present in grossly measurable quantities in the stools of normal young children, and smaller but detectable quantities are present in normal adult stools. Lipases, including esterases that hydrolyze dietary triglycerides, are also found in normal stools and are capable of hydrolizing triglycerides and other glycerides found in human skin to form irritating fatty acid and glycerol by-products. Thus, when skin is exposed to enzymes such as lipases and proteases present in body exudates, lipid-containing components and protein-containing components of the skin, especially of the barrier layer (stratum corneum), can be broken down resulting in the irritation and inflammation of diaper rash. Moreover, perturbation of the skin barrier allows other components of urine and feces, ammonia, bacteria and the like which may not otherwise be irritating by themselves, to migrate through the compromised skin barrier to produce additional irritation and possible infection.

It is known that bile salts are also present in body exudates. These bile salts are known normally to emulsify lipids in the body to ensure that the lipase enzymes are capable of performing at the lipid/water interface. Bile salts are also active when excreted in feces and other exudates and are available to act as coenzymes and enhance the activity of lipases that attack lipids in the stratum corneum of the skin that is exposed to body exudates.

The irritating effects of fecal enzymatic activity toward the skin are likely to be amplified if urine is present and/or if the skin is occluded. The production of ammonium hydroxide by the action of the bacterial enzyme urease on urine results in an increase in pH, for example to levels of 7.0 and above, at which the enzymatic activity of proteases and other enzymes such as lipases present in feces is enhanced. For example, the optimal pH range for urease activity is 6.4–6.9, for trypsin 7.8–8.2, and for lipases 7.5–9.5. At a pH greater than 7.0, free ammonia is released from urine as a toxic additional skin irritant. Urine itself can also contribute to diaper rash by adding moisture to the diaper environment. Water, and particularly water in the form of urine, is especially effective at diminishing the barrier property of skin, thereby enhancing the susceptibility of skin to fecal enzyme irritation. Since urine and feces are commonly present in the absorbent article at the same time, and exposure to the skin for several hours is not uncommon, suitable conditions and ample time are available for this interaction and the resulting skin damage to occur. An alkaline feces pH is a further contributing factor to enhanced enzymatic activity of feces. For example, it is well known that although the feces of breast-fed babies are usually acidic, the feces of bottle-fed and spoon-fed infants are generally alkaline, with a pH ranging from slightly alkaline (pH 7.2–7.5) to very alkaline (pH 8.7 and above). Thus, bottle-fed and spoon-fed infants in particular may have a propensity to develop diaper rash due to pH-enhanced activity of fecal enzymes.

In view of the contribution of alkaline pH to enhanced fecal enzyme activity, several attempts have been made to maintain skin pH by the use of pH control agents, such as buffering agents or weak acids, in the absorbent article or as ingredients in topically applied skin care products. It is thought that effectively maintaining skin pH in its natural acidic state (i.e., about 3.0 to about 5.5) may counteract the irritating effects of ammonia and reduce the activity of fecal enzymes. Reducing the enzymatic activity on the skin by this approach, however, is potentially difficult in the situation where feces are deposited directly on the skin following a bowel movement.

Certain anti-enzyme compounds have been included in topically applied compositions for treatment or prevention of diaper rash caused by the prolonged contact of human skin with body wastes. For example, U.S. Pat. No. 4,556,560 describes compositions containing water-soluble lipase inhibitors that are preferably metallic salts such as zinc chloride in a barrier-like carrier such as polyethylene glycol. If incorporated into a diaper topsheet or absorbent core, the lipase inhibitor is preferably in an aqueous or volatile carrier such as ethanol for transfer to the skin when the diaper is wetted with urine. U.S. Pat. No. 5,091,193 describes compositions for application to the skin at the time of diaper change that contain a chelating agent, such as phytic acid, ethylenediamine tetraacetic acid (EDTA), and the like, that restricts the availability of metals that ureases and proteases require as cofactors for activity. The composition may further include a lipase substrate such as an ester of a fatty alcohol or an additional anti-enzyme, such as a saturated or unsaturated, linear or branched, zinc salt of a fatty acid of 2 to 22 carbon atoms or an aminated acylated acid such as propionylcysteine, propionylhydroxyproline or caproylcysteine.

While compositions for the treatment of diaper rash have been described that include certain inhibitors of enzyme activity, there has been no previous description of a regimen for treatment or prevention of diaper dermatitis by which skin care compositions containing enzyme inhibitors are included in absorbent articles for automatic transfer to the skin of a wearer during normal wear of a treated article, or that the use, preferably the repeated use, of such absorbent articles automatically transfers sufficient levels of the enzyme inhibitors to selected regions of the wearer's skin to provide a defense against fecal penetration and enzymatic activity. Moreover, there has been no previous description of absorbent articles having a skin care composition containing an enzyme inhibitor immobilized (at room temperature) on a wearer-contacting surface, preferably a topsheet, wherein the skin care composition and enzyme inhibitor are transferred to the skin of the wearer when the skin care composition is warmed to body temperature.

SUMMARY OF THE INVENTION

The invention provides an absorbent article, at least a portion of which comprises a skin care composition that comprises an enzyme inhibitor, wherein the skin care composition, including the enzyme inhibitor, is at least partially transferred from the article to the skin of a wearer of the article as a result of normal contact, wearer motion and/or body heat. The enzyme inhibitor is any material that inhibits the activity of one or more enzymes, preferably at an IC50, as measured by the General Fecal Enzymes Method defined below, of not more than about 500 micromolar ($\mu M$).

Suitable enzyme inhibitors for use in the article of the invention include, but are not limited to, protease inhibitors, lipase inhibitors, elastase inhibitors, urease inhibitors, amylase inhibitors, and the like, and further include inactivators of bile salts which otherwise would act as cofactors for lipase activity. The skin care composition preferably comprises about 0.001% to about 50% of the enzyme inhibitor, typically about 0.01% to about 25%, more typically about 0.1% to about 10%, and most typically about 0.1% to about 5%.

The nature of the skin care composition comprising the enzyme inhibitor may vary widely, but in one preferred embodiment is solid or semi-solid at room temperature (20° C.). In a particularly preferred embodiment, the skin care composition will further comprise about 5% to about 95% of an emollient having a plastic or fluid consistency at 20° C. Most preferably, the skin care composition further comprises about 5% to about 95% of an agent that is capable of immobilizing the emollient in the article and that has a melting point of at least about 35° C. Preferably, the portion of the absorbent article incorporating the skin care composition comprising the enzyme inhibitor is a wearer-contacting surface, which is more preferably a liquid pervious topsheet.

Since the enzyme inhibitor is transferred to the skin with the skin care composition, the inhibitor is available at the skin/urine and skin/feces interfaces to inhibit enzymatic activity on the skin and reduce or prevent the occurrence of inflammation. Repeated application of similar treated articles to the wearer's skin provides an available source with which the enzyme inhibitor transfers onto the skin continuously over time and accumulates to provide a proactive defense against harmful enzymes for the treatment and/or prevention of diaper dermatitis.

DETAILED DESCRIPTION OF THE INVENTION

I. Definitions

Figure 1:
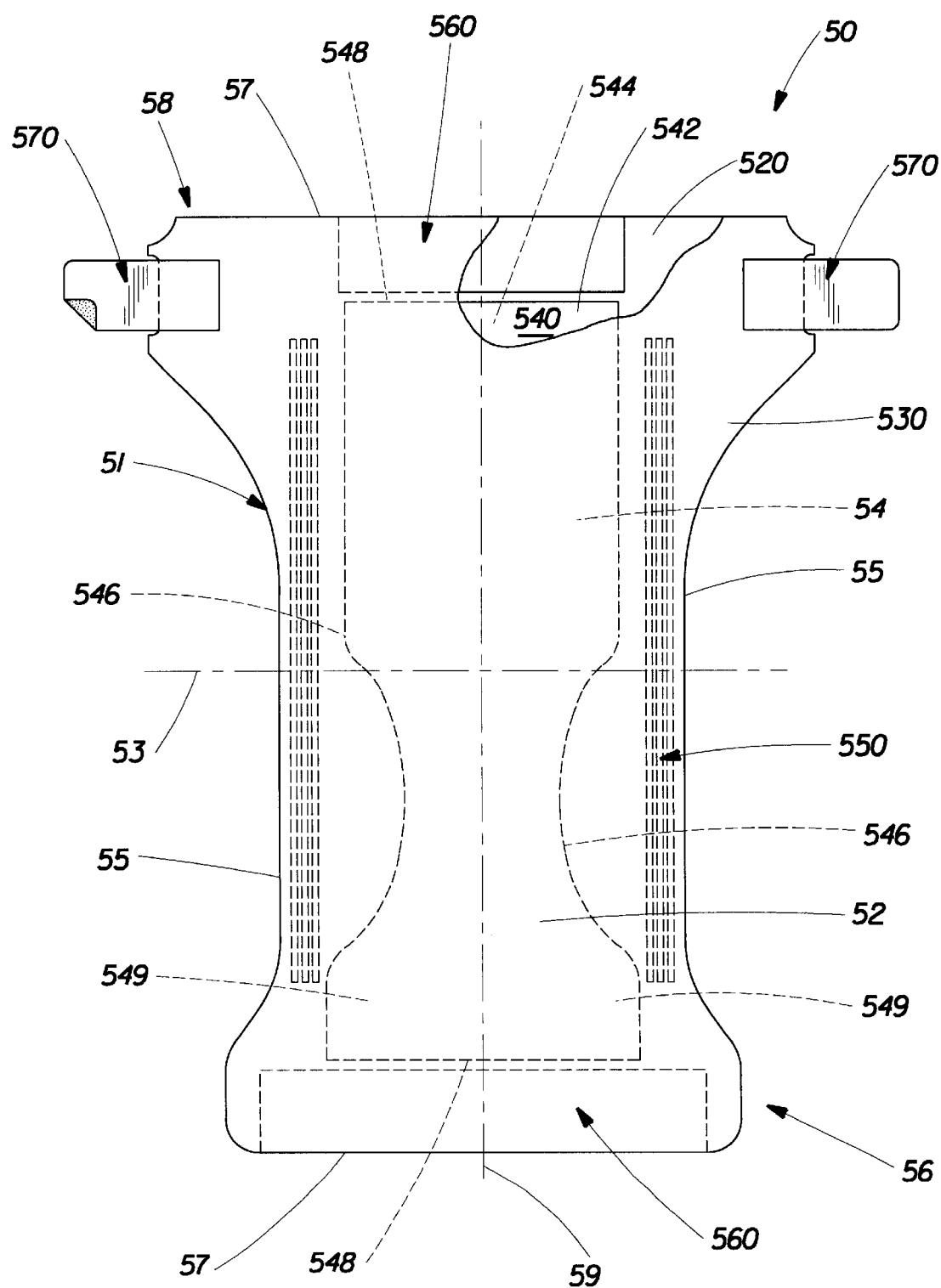
FIG. 1 is a schematic illustration of an absorbent article in the form of a diaper according to the present invention.

As used herein, the term "comprising" means that the various components, ingredients, or steps can be conjointly employed in practicing the present invention. Accordingly, the term "comprising" encompasses the more restrictive terms "consisting essentially of" and "consisting of".

As used herein, the term "treated article" means an absorbent article having a skin care composition on or migratable to at least one wearer-contacting surface of that article.

As used herein, the term "wearer-contacting surface" of an absorbent article is one or more surfaces of any article components that contact the wearer at some time during the wear period. Wearer contact surfaces include, but are not limited to, portions of the topsheet, leg cuffs, waist region, side panels, fastening tabs, and the like, which contact a wearer during use.

As used herein, the term "skin care composition" refers to any composition containing an enzyme inhibitor which is transferred to the skin of a wearer of a treated article as a result of normal contact, wearer motion and/or body heat when the article is being worn.

As used herein, the term "$IC_{50}$" means the inhibitory concentration (e.g., a micromolar concentration, AM) of a substance (inhibitor) which reduces the rate of substrate cleavage by an enzyme by 50%, as measured by the standard in vitro enzyme activity assays described below. The $IC_{50}$ is calculated according to the equation $IC_{50}=[I]/[(v/vi)-1]$, where [I] is the inhibitor concentration tested, v is the rate of substrate cleavage in the absence of the inhibitor and vi is the rate of substrate cleavage in the presence of the inhibitor. As described further below, the IC50 of an enzyme inhibitor according to the invention may be measured by a Purified Enzyme method, by a Specific Fecal Enzyme method or by a General Fecal Enzymes method.

Other terms are defined herein where initially discussed.

All percentages, ratios and proportions used herein are by weight unless otherwise specified.

II. Enzyme Inhibitors

Inhibitors of enzyme activity are well known and are typically classified as competitive inhibitors (which compete with the substrate for binding at the active site on the enzyme) and non-competitive inhibitors (which bind to a site other than the active site to inactivate the enzyme). Many enzymes, such as metalloproteases, are inhibited by substances that bind with a metal group on the enzyme. Chelating agents are effective inhibitors of other enzymes that require the presence of metal ions, such as the ions of calcium, cobalt, copper, magnesium, manganese, sodium, potassium, or zinc, for activation. Since enzymes are proteins, antibodies raised against specific enzymes are also effective enzyme inhibitors.

Enzyme inhibitors useful in the absorbent articles described herein will typically have an IC50 value of not more than about 500 $\mu$M, more typically not more than about 250 $\mu$M, still more typically not more than about 100 $\mu$M, and still more typically not more than about 50 $\mu$M. It will be understood that certain enzyme inhibitors (e.g., EDTA) will have higher IC50 values but will still be useful in the absorbent articles described herein. For materials for which the molecular weight cannot be determined, such materials will typically reduce enzyme activity by at least 50% at a concentration in the skin care composition of not more than about 5 percent by weight. Representative methods for measuring enzyme inhibitory activity are discussed below.

Without limitation, any type of enzyme inhibitor may be employed in the skin care compositions transferable to the wearer's skin from the absorbent articles of the present invention, including any naturally occurring inhibitor of plant, microbial and/or animal origin (including human) and synthetically manufactured chemical inhibitor. The enzyme inhibitors may be hydrophilic or hydrophobic in nature and may thus be water soluble or soluble in a hydrophobic vehicle. The enzyme inhibitors are preferably present in the skin care composition in a concentration of about 0.001% to about 50% by weight, typically about 0.01% to about 25%, more typically about 0.1% to about 10%, and most typically about 0.1% to about 5%. Because of the variety of enzyme inhibitors employed in the invention, the effective concentration of each inhibitor must be separately determined, as known to those skilled in the art.

The enzyme inhibitors may be employed singly or as a mixture of enzyme inhibitors such as a "cocktail" of inhibitors in a single absorbent article. Moreover, different enzyme inhibitors may be employed in skin care compositions in different locations in a single absorbent article.

Because of the wide diversity of enzymes present in feces and other body exudates, it is reasonably predictable that materials such as those described below which inhibit certain classes of enzymes (e.g., proteases) may also inhibit enzymes which cleave substrates other than those specified (e.g., proteins and peptides). Hence, inhibitors which inhibit proteases may also inhibit lipases and other esterases, amylases and/or ureases and vice versa.

Inhibitors of enzymes and/or coenzymes most frequently found in feces or other body exudates are preferred in the skin care compositions in the invention absorbent articles. Thus, the enzyme inhibitors are preferably inhibitors of proteolytic enzymes such as trypsin, chymotrypsin, aminopeptidase and elastase; lipases; bile salts; amylases; and/or ureases.

Exemplary suitable inhibitors of proteases for use in the invention that are believed to inhibit the type of protease indicated in parentheses include, but are not limited to, soybean trypsin inhibitor and other plant-derived trypsin inhibitors such as lima bean protease inhibitor, corn protease inhibitor and the like; Bowman-Birk inhibitor (serine, trypsin-like protease inhibitor); pancreatic trypsin inhibitor such as bovine pancreatic basic trypsin inhibitor and other animal-derived pancreatic trypsin inhibitors; egg white trypsin inhibitor (serine, trypsin-like protease inhibitor); ovomucoids containing ovoinhibitors such as from chicken or turkey egg white (trypsin and chymotrypsin inhibitors); chymostatin (serine, chymotrypsin-like protease inhibitor); aprotinin (serine protease inhibitor); leupeptin and its analogs such as propionyl-leupeptin, N-$\alpha$-t-BOC-deacetylleupeptin (serine and cysteine protease inhibitor); bestatin and its analogs such as epibestatin and nitrobestatin (aminopeptidase metalloprotease inhibitor); amastatin and its analogs such as epiamastatin (aminopeptidase inhibitor); antipain (trypsin inhibitor); antithrombin III (serine protease inhibitor); hirudin (thrombin-like serine protease inhibitor); cystatin (egg white cysteine protease inhibitor); E-64 (trans-epoxysuccinyl-L-leucylamido-(4-guanidino)-butane) and its analogs (cysteine protease inhibitor); $\alpha_2$-macroglobulin (universal endoprotease inhibitor); $\alpha_1$-antitrypsin (trypsin inhibitor); pepstatin and its analogs such as acetyl pepstatin, pepstatin A, NIe-Sta-Ala-Sta (aspartyl protease inhibitor); apstatin (aminopeptidase P inhibitor); (2R)-2-mercaptomethyl-4-methylpentanoyl-b-(2-naphthyl)-Ala-Ala amide (matrix metalloprotease inhibitor); (2R)-2-mercaptomethyl-4-methylpentanoyl-Phe-Ala amide (matrix metalloprotease inhibitor); N-acetyl-Leu-Leu-methioninal (calpain inhibitor); N-acetyl-Leu-Leu-norleucinal (calpain inhibitor); p-aminobenzyol-Gly-Pro-D-Leu-D-Ala hydroxamic acid (matrix metalloprotease inhibitor); 2(R)-[N-(4-methoxyphenylsulfonyl)-N-(3-pyridylmethyl)amino]-3-methylbutano-hydroxamic acid (metalloprotease inhibitor); L-1-chloro-3-[4-tosylamido]-7-amino-2-heptanone-HCl (TLCK), L-1-chloro-3-[4-tosylamido]-4-phenyl-2-butanone (TPCK), tranexamic acid, glycyrrhizic acid, 18-$\beta$-glycyrrhetinic acid, and corresponding salts, stearylglycyrrhetinate, colloidal oat extracts, elhibin, zinc salts, iodoacetate, phenylmethylsulfonyl fluoride, phosphoramidon, 4-(2-aminoethyl)-benzenesulfonylfluoride HCl, 3,4-dichloroiso-coumarin, quercetin, and the like, and mixtures thereof.

Chelating agents have also been found to be useful as inhibitors of both proteases and ureases at a concentration of about 0.1% to about 2%. Exemplary chelating agents are phytic acid, nitrilotriacetic acid, EDTA, diethylene triamino pentacetic acid, hyroxyethyl ethylene diamine triacetic acid, and the corresponding salts, disclosed in U.S. Pat. No.

5,091,193 issued to Enjolras on Feb. 25, 1992, the disclosure of which is hereby incorporated by reference.

Among preferred protease inhibitors for use in the absorbent articles of the invention are compounds that exhibit inhibitory activity that is not necessarily restricted to a single class of proteases. Such compounds include, but are not limited to, hexamidine and its salts; pentamidine and its salts; benzamidine and its salts and derivatives, p-aminobenzamidine and its salts and derivatives; and guanidinobenzoic acid and its salts and derivatives such as those disclosed in U.S. Pat. No. 5,376,655 issued to Imaki et al. on Dec. 27, 1994, the disclosure of which is hereby incorporated by reference. Other preferred protease inhibitors include polymer derivatives of guanidinobenzoic acid disclosed and made in our co-pending U.S. patent application Ser. No. 09/041,196, filed Mar. 12, 1998, in the name of T. L. Underiner et al, co-filed with the present application, the disclosure of which co-pending application is hereby incorporated by reference.

Protease inhibitors that are preferred in the practice of the invention are soybean trypsin inhibitor, aprotinin, hexamidine (e.g., hexamidine diisethionate), p-aminobenzamidine, leupeptin, pepstatin A, chymostatin and polymer derivatives of guanidinobenzoic acid (disclosed and made in our copending U.S. patent application Ser. No. 09/041,196, incorporated by reference above). Particularly preferred protease inhibitors are soybean trypsin inhibitor, hexamidine, p-aminobenzamidine and the foregoing polymer derivatives of guanidinobenzoic acid.

Ureases are known to be inhibited in the presence of trace amounts of heavy metal ions, such as those of silver, copper, and the like. Thus, trace amounts (as little as 0.001% or less) of salts of these metals are useful as urease inhibitors. Other exemplary inhibitors of urease activity include, but are not limited to, acetyl hydroxamic acid and its derivatives, such as cinnamoyl hydroxamic acid and other alkyl hydroxamic acids, corresponding salts and derivatives; phosphoramidate and its derivatives. Such compounds are competitive inhibitors of urease at a concentration of about 2 micromolar ($\mu$M). Chelating agents have also been found to be useful as inhibitors of both proteases and ureases at a concentration of about 0.1% to about 2%. Exemplary chelating agents are phytic acid, nitrilotriacetic acid, ethylenediamine tetraacetic acid (EDTA), diethylene triamino pentacetic acid, hyroxyethyl ethylene diamine triacetic acid, and the corresponding salts, disclosed in U.S. Pat. No. 5,091,193 incorporated by reference above. Other urease inhibiting compounds are disclosed in U.S. Pat. No. 3,935,862 issued to Kraskin on Feb. 3, 1976, the disclosure of which is hereby incorporated by reference, and include amino acid compounds, such as hydroxyalkylamino acids, sulfhydryl amino acids, aminosulfonic acids, aminophosphonic acid compounds and ether amino acids such as methoxyethyliminodiacetic acid, ethylene-bis-(oxypropylaminodiacetic acid), ethylene-bis-(oxyethyliminodiacetic acid), amino-methyl phosphonic acid (N,N-diacetic acid), and the like, and aminopolycarboxylic acid compounds. including acids and salts diethylenetri-aminepentaacetic acid (DTPA), N-hydroxyethylethylenediaminetriacetic acid (HEDTA), and the like.

Other suitable inhibitors of urease are disclosed in U.S. Pat. No. 5,409,903 issued to Polak et al. on Apr. 25, 1995, the disclosure of which is hereby incorporated by reference. This patent discloses dibasic magnesium phosphate, dialdehyde polysaccharides and zeolite, used alone in combination with each other or with the calcium compounds, calcium acetate, calcium chloride, calcium gluconate and calcium lactate as well as the magnesium compounds, magnesium chloride and magnesium citrate, for inhibition of ureases.

Suitable lipase inhibitors include, but are not limited to, water soluble salts of metals, such as cadmium, cobalt, copper, iron, molybdenum, silver, lanthanum, tin and zinc. Exemplary lipase inhibiting compounds are disclosed in U.S. Pat. No. 4,556,560, hereby incorporated by reference, and include zinc chloride, zinc acetate, zinc nitrate trihydrate, zinc nitrate hexahydrate, zinc sulfate, zinc sulfate heptahydrate, zinc sulfate hexahydrate, iron(II) chloride, iron(II) chloride tetrahydrate, iron(III) chloride, iron(III) chloride monohydrate, iron(III) chloride hexahydrate, iron (II) lactate, iron(III) lactate, iron(III) malate, iron(II) nitrate, iron(III) nitrate hexahydrate, iron(III) nitrate.9$H_2$O, iron(II) sulfate and its hydrates, iron(III) sulfate and its hydrates, copper sulfate pentahydrate, tin chloride, cobalt chloride and lanthanum chloride, zinc salts of both saturated and unsaturated monocarboxylic acids having about 6 to about 12 carbon atoms, block copolymers of propylene oxide and ethylene oxide (e.g., marketed as Pluronic® and Tetronic® by BASF Corp.), glycerol triesters of fatty acids having from about 2 to about 20 carbons such as triacetin, and the like. Other useful lipase inhibitors are disclosed in U.S. Pat. No. 5,091,193, hereby incorporated by reference, and include esters of fatty alcohols, such as saturated or unsaturated, linear or branched alkyl acetate, lactate or propionate containing 10 to 20 carbon atoms; saturated or unsaturated, linear or branched zinc salts of fatty acids of 2 to 22 carbon atoms, such as those formed with propionic acid isobutyric acid, caproic acid, undecylenic acid, and the like; zinc salts of aminated acylated acids, such as propionylcysteine, propionyl-hydroxyproline or caproylcysteine, and the like. Lipase inhibitors, such as the foregoing, have been found to be useful at a concentration of about 0.01% to about 10%.

Still other useful lipase inhibitors, disclosed in our copending Patent Application EP 97/120,699, filed Nov. 26, 1997 in the name of G. Palumbo et al., the disclosure of which is hereby incorporated by reference, include specific ester compounds that act as a substitute substrate for fecal lipases and thereby are competitive lipase inhibitors. These esters have the formulas:

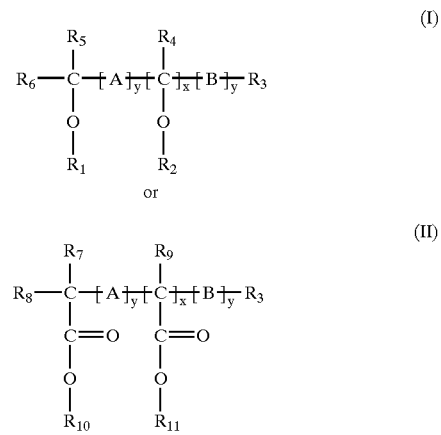

wherein $R_1$ and each $R_2$ independently are an acyl group with from 2 to 22 carbon atoms, or an alkyl, alkenyl, arylalkyl, hydroxyalkyl group with from 1 to 24 carbon atoms or hydrogen, whereby at least one of $R_1$ and $R_2$ is such an acyl group, $R_3$, $R_4$, $R_5$, $R_6$, $R_7$, $R_8$, and $R_9$ are independently an alkyl, alkenyl, arylalkyl, hydroxyalkyl, alkoxy groups of from 1 to 24 carbon atoms, hydroxy group or hydrogen; $R_{10}$ and $R_{11}$ are independently an alkyl, alkenyl, arylalkyl, hydroxyalkyl, alkoxy groups of from 2 to 24 carbon atoms, hydroxy group or hydrogen; A and B are independently a $C_1$–$C_6$ linear or branched alkylene, alkenylene, alkoxylene, hydroxyalkylene groups; the values of x are independently from 0 to 15; the values of y are independently 0 or 1, with the proviso that when x=2 and y=0, at least one $R_2$ is an alkyl, alkenyl, arylalkyl, hydroxyalkyl group with from 1 to 24 carbon atoms or hydrogen.

Still further examples of lipase inhibitors are those disclosed in U.S. Pat. No. 5,643,874, hereby incorporated by reference, which include: (2S,3S,5S)-5-[(S)-2-formamido-4-methyl-valeryloxy]-2-hexyl-3-hydroxy-hexadecanoic 1,3 acid lactone, also known as tetrahydrolipstatin; (2S,3S,5S, 7Z, 10Z)-5-[(S)-2-formamido-4-methyl-valeryloxy]-2-hexyl-3-hydroxy-7,10-hexadecadienoic 1,3 acid lactone, also known as lipstatin;1-(trans-4-isobutylcyclohexyl)-2-(phenylsulfonyloxy)ethanone, also known as FL-386; 4-methylpiperidine-1-carboxylic acid 4-phenoxyphenyl ester, also known as WAY-121898; N-[3-chloro-4-(trifluoromethyl)phenyl-]N'-[3-(trifluoromethyl)-phenyl] urea, also known as BAY-N-3176; N-formyl-L-valine-(S)-1-[[(2S, 3S)-3-hexyl-4-oxo-2-oxetanyl]methyl]hexyl ester, also known as valilactone; (2S,3S,5S,7Z, 10Z)-5-[(S)-2-acetamido-3-carbamoylpropionyloxy]-2-hexyl-3-hydroxy-7,10-hexadecadienoic lactone, also known as esterastin; (3S,4S)-4-[(1S,5R,7S,8R,9R,E)-8-hydroxy 1,3,5,7,9-pentamethyl-6-oxo-3-undecenyl]-3-methyl-2-oxetanone, also known as ebelactone A; (3S,4S)-3-ethyl-4-[(1S,5R,7S, 8R,9R,E)-8-hydroxy-1,3,5,7,9-pentamethyl-6-oxo-3-undecenyl]-2-oxetanone, also known as ebelactone B; and 1,6-di(O-(carbamoyl)cyclohexanone oxime)hexane, also known as RHC 80267.

Exemplary inhibitors of bile salts that are coenzymes for lipolytic enzymes and are useful as lipase enzyme inhibitors in the absorbent articles of the invention include, but are not limited to, cationic compounds disclosed in our copending Patent Application EP 97/120,700, filed Nov. 26, 1997 in the name of G. Palumbo et al., the disclosure of which is hereby incorporated by reference. Such compounds have the formulas:

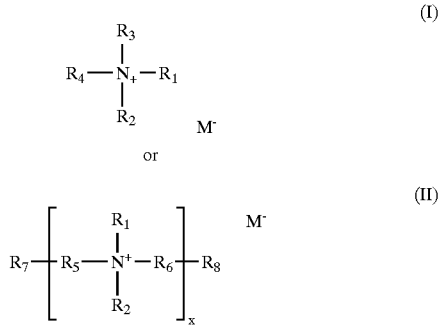

or an amphoteric compound and preferably an acidity source, the amphoteric compound having at its iso-electric point the formula:

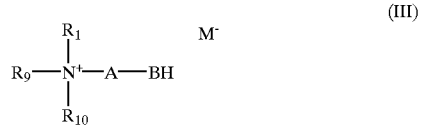

for preparation of a composition for treatment, prevention or reduction of lipolytic dermatitis of the external skin, wherein $R_1$, $R_2$, $R_3$ and $R_4$ are independently a $C_1$–$C_{22}$ alkyl, alkenyl, aryl, arylalkyl, amidoalkyl, (poly) alkoxy, hydroxyalkyl, or acyl groups, or two or more groups of $R_1$, $R_2$, $R_3$ and $R_4$ form together one or more ring structures; $R_5$, $R_6$ and A are independently a $C_1$–$C_{22}$ alkylene, alkenylene, (poly) alkoxylene, hydroxyalkylene, arylalkylene or amido alkylene groups; $R_7$ and $R_8$ are independently a $C_1$–$C_4$ alkyl, alkenyl, alkoxy group or a hydroxy group or hydrogen; $R_9$ and $R_{10}$ are independently a $C_1$–$C_{22}$ alkyl, alkenyl, aryl, arylalkyl, amidoalkyl, (poly) alkoxy, hydroxyalkyl, or acyl groups, or two or more of the groups $R_1$, $R_9$ and $R_{10}$ form together one or more ring structures; BH is a proton donating group; x is from 2 to 4; and M- is a counter ion.

Another exemplary suitable bile salt inhibitor is cholestyramine, described in a publication by C. Michael White et al., entitled "Cholestyramine Ointment to Treat Buttocks Rash and Anal Excoriation in an Infant", The Annals of Pharmacotherapy 30: 954–956, September 1996.

Derivatives of p-guanidinobenzoic acid, especially esters of p-guanidinobenzoic acid, have been described as inhibitors of esterases. Such inhibitors are useful in the skin care compositions of the absorbent articles of the invention, and are disclosed in U.S. Pat. No. 5,376,655 issued to Imaki et al. on Dec. 27, 1994, the disclosure of which is hereby incorporated by reference.

Suitable amylase inhibitors and/or glucosidase amylase inhibitors include those disclosed in U.S. Pat. No. 5,643, 874, hereby incorporated by reference, and include O-4,6-dideoxy-4-[[[1S-(1α,4α,5β,6α)]-4,5,6-trihydroxy-3-(hydroxymethyl)-2-cyclohexen-1-yl]amino]-α-D-glucopyranosyl-(1→4)O-α-D-glucopyranosyl-(1→4)-D-glucose, also known as acarbose; 2(S),3(R),4(S),5(S)-tetrahydroxy-N-[2-hydroxy-1-(hydroxymethyl)-ethyl]-5-(hydroxymethyl)-1(S)-cyclohexamine, also known as voglibose;1,5-dideoxy-1,5-[(2-hydroxyethyl)imino]-D-glucitol, also known as miglitol; 1,5-dideoxy-1,5-[2-(4-ethoxycarbonylphenoxy)-ethylimino]-D-glucitol, also known as emiglitate; 2,6-dideoxy-2,6-imino-7-(β-D-glucopyranosyl)-D-glycero-L-guloheptitol, also known as MDL-25637; 1,5-dideoxy-1,5-(6-deoxy-1-O-methyl-α-D-glucopyranos-6-ylimino)-D-glucitol, also known as camiglibose;1,5,9,11,14-pentahydroxy-3-methyl-8,13-dioxo-5,6,8,13-tetrahydrobenzo[a]-naphthacene-2-carboxylic acid, also known pradimicin Q; also known as adiposine; and 1,2-dideoxy-2-[2(S),3(S),4(R)-trihydroxy-5-(hydroxymethyl)-5-cyclohexen-1(S)-ylamino]-L-glucopyranose, also known as salbostatin. Other suitable amylase inhibitors include tendamistat, trestatins, and those derived from plants, especially from wheat, rice, maize, barley and other cereal grains, beans, and seaweed.

III. Absorbent Articles

As used herein, the term "absorbent article" refers to a device which absorbs and retains body exudates. The term "disposable" is used herein to describe absorbent articles which are not intended to be laundered or otherwise restored or reused as an absorbent article after a single use. Examples of disposable absorbent articles include feminine hygiene garments such as sanitary napkins, panty liners and tampons, diapers, incontinence briefs, incontinence pads, diaper holders, training pants, and the like.

Disposable absorbent articles typically comprise a liquid pervious topsheet, a liquid impervious backsheet and an absorbent core positioned between the topsheet and the backsheet. Disposable absorbent articles and components thereof, including the topsheet, backsheet, absorbent core, and any individual layers of these components, have a body facing surface and a garment-facing surface. As used herein "body facing surface" means that surface of the article or component which is intended to be worn toward or adjacent to the body of the wearer, while the "garment facing surface" is on the opposite side and is intended to be worn toward or placed adjacent to the wearer's clothing or undergarments when the disposable absorbent article is worn.

The following description generally discusses the absorbent core, topsheet, and backsheet materials that are useful in disposable absorbent articles. It is to be understood that this general description applies to these components of the specific absorbent articles shown in FIG. 1 and further described below, in addition to those of other disposable absorbent articles which are generally described herein.

In general, the absorbent core is capable of absorbing or retaining liquids (e.g., menses, urine, and/or other body exudates). The absorbent core is preferably compressible, conformable, and non-irritating to the wearer's skin. The absorbent core may be manufactured in a wide variety of sizes and shapes (e.g., rectangular, oval, hourglass, "T" shaped, dog bone, asymmetric, etc.). In addition to absorbent composites, the absorbent core may include any of a wide variety of liquid-absorbent materials commonly used in absorbent articles, such as comminuted wood pulp, which is generally referred to as airfelt. Examples of other suitable absorbent materials for use in the absorbent core include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers including composites; absorbent gelling materials; or any equivalent material or combinations of materials, or mixtures of these.

The configuration and construction of the absorbent core may be varied (e.g., the absorbent core may have varying caliper zones and/or have a profile so as to be thicker in the center; hydrophilic gradients; gradients of absorbent composites; superabsorbent gradients; or lower average density and lower average basis weight zones, e.g., acquisition zones; or may comprise one or more layers or structures). The total absorbent capacity of the absorbent core should however, be compatible with the design loading and the intended use of the absorbent article. Further, the size and absorbent capacity of the absorbent core may be varied to accommodate different uses such as diapers, incontinence pads, panty liners, regular sanitary napkins, and overnight sanitary napkins, and to accommodate wearers ranging from infants to adults. The absorbent core can also include other absorbent components that are often used in absorbent articles, for example, a dusting layer, a wicking or acquisition layer such as a high loft acquisition layer for temporary holding of urine, or a secondary topsheet for increasing the wearer's comfort.

The topsheet is preferably compliant, soft feeling, and non-irritating to the wearer's skin. Further, the topsheet is liquid pervious, permitting liquids (e.g., menses and/or urine) to readily penetrate through its thickness. A suitable topsheet may be manufactured from a wide range of materials such as woven and nonwoven materials (e.g., a nonwoven web of fibers), including apertured nonwovens; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, spuniace carded, wet-laid, melt-blown, hydroentangled, hydroformed, hydroapertured, combinations of the above, or the like. Whether comprised of a woven or nonwoven material, the topsheet preferably comprises a skin care composition containing a enzyme inhibitor, as described further below.

The backsheet is impervious to liquids (e.g., menses and/or urine) and preferably comprises a thin plastic film, although other flexible liquid impervious materials may also be used. As used herein, the term "flexible" refers to materials which are compliant and will readily conform to the general shape and contours of the human body. The backsheet prevents the exudates absorbed and contained in the absorbent core from wetting articles which contact the absorbent article such as bedsheets, pants, pajamas and undergarments. The backsheet may thus comprise a woven or nonwoven material, polymeric films such as thermoplastic films of polyethylene or polypropylene, or composite materials such as a film-coated nonwoven material. A suitable backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. The backsheet is preferably embossed and/or matte finished to provide a more clothlike appearance. Further, the backsheet may permit vapors to escape from the absorbent core (i.e., the backsheet is breathable) while still preventing exudates from passing through the backsheet. The size of the backsheet is dictated by the size of the absorbent core and the exact absorbent article design selected.

The backsheet and the topsheet are positioned adjacent the garment facing surface and the body facing surface, respectively, of the absorbent core. The absorbent core is preferably joined with the topsheet, the backsheet, or both in any manner as is known by attachment means (not shown in FIG. 1) such as those well known in the art. However, embodiments of the absorbent articles are envisioned wherein portions or the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern as illustrated by the apparatus and method shown in U.S. Pat. No. 3,911,173, issued to Sprague, Jr. on Oct. 7, 1975; U.S. Pat. No. 4,785,996, issued to Zwieker et al. on Nov. 22, 1978; and U.S. Pat. No. 4,842,666, issued to Werenicz on Jun. 27, 1989. Each of these patents is incorporated herein by reference. Alternatively, the attachment means may comprise heat bonds, pressure bonds, ultrasonic bonds, dynamic mechanical bonds, or any other suitable attachment means or combinations of these attachment means as are known in the art.

A preferred disposable absorbent article of the invention, at least a portion of which has a enzyme inhibitor incorporated therein and, more preferably, has a wearer-contacting surface treated with a skin care composition containing a enzyme inhibitor, is a diaper. As used herein, the term "diaper" refers to an absorbent article generally worn by infants, and incontinent persons, that is worn about the lower torso of the wearer. In other words, the term "diaper" includes infant diapers, training pants, adult incontinence devices and the like.

FIG. 1 is a plan view of the diaper 50 useful in the invention in its flat-out, uncontracted state (i.e., with elastic induced contraction pulled out) with portions of the structure being cut-away to more clearly show the construction of the diaper 50 and with the portion of the diaper 50 which faces away from the wearer (the outer surface) oriented towards the viewer. As shown in FIG. 1, the diaper 50 preferably comprises a liquid pervious topsheet 520, a liquid impervious backsheet 530 joined with the topsheet 520, an absorbent core 540 positioned between the topsheet 520 and the backsheet 530, the absorbent core 540 having a garment facing surface 542, a body facing surface 544, side edges 546, waist edges 548, and ears 549. The diaper 50 preferably further comprises elasticized leg cuffs 550, and elastic waist feature multiply designed as 560, and a fastening system generally multiply designed as 570.

The diaper 50 is shown in FIG. 1 to have an outer surface 52, an inner surface 54 corresponding to the body facing surface which is opposed to the outer surface 52, a first waist region 56, a second waist region 58, and a periphery 51 which is defined by the outer edges of the diaper 50 in which the longitudinal edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The body-facing surface 54 of the diaper 50 comprises that portion of the diaper 50 which is positioned adjacent to the wearer's body during use. The body facing surface 54 generally is formed by at least a portion of the topsheet 520 and other components that may be joined to the topsheet 520, such as leg cuffs 550, as well as any regions to which the topsheet may not extend but which still contact the wearer, such as the waist feature 560, side panels, and the like. The outer surface 52 comprises that portion of the diaper 50 which is positioned away from the wearer's body (i.e., the outer surface 52 generally is formed by at least a portion of the backsheet 530 and other components that may be joined to the backsheet 530). The first waist region 56 and the second waist region 58 extend, respectively, from the end edges 57 of the periphery 51 to the lateral centerline 53 of the diaper 50. FIG. 1 also shows the longitudinal centerline 59.

FIG. 1 shows a preferred embodiment of the diaper 50 in which the topsheet 520 and the backsheet 530 have length and width dimensions generally larger than those of the absorbent core 540. The elasticized leg cuffs 550 and the backsheet 530 extend beyond the edges of the absorbent core 540 to thereby form the periphery 51 of the diaper 50.

Diapers of the present invention can have a number of well-known configurations, with the absorbent cores thereof being adapted to the present invention. Exemplary configurations are described generally in U.S. Pat. No. 3,860,003, issued to Buell on Jan. 14, 1975; U.S. Pat. No. 5,151,092, issued to Buell et al. on Sep. 29, 1992; U.S. Pat. No. 5,221,274 issued to Buell et al. on Jun. 22, 1993. Each of these patents is incorporated herein by reference. Another diaper configuration to which the present invention can be readily adapted is described in U.S. Pat. No. 5,554,145 issued to Roe et al., the disclosure of which is incorporated herein by reference.

A topsheet 520 which is particularly suitable for use in the diaper 50, is carded and thermally bonded by means well known to those skilled in the fabrics art. A satisfactory topsheet for the present invention comprises staple length polypropylene fibers having a denier of about 2.2 As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 520 of diaper 50 is preferably made of a hydrophilic material to promote rapid transfer of liquids (e.g., urine) through the topsheet. If the topsheet is made of a hydrophobic material, at least portions of the upper surface of the topsheet are treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. Nos. 4,988,344 and 4,988,345, both issued to Reising, et al. on Jan. 29, 1991, each of which is incorporated by reference herein.

Alternatively, the topsheet may be in the form of an apertured formed film, which is preferred in feminine hygiene absorbent articles. Apertured formed films are useful because they are pervious to body liquids and yet non-absorbent and have a reduced tendency to allow liquids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 issued to Thompson on Dec. 30, 1975; U.S. Pat. No. 4,324,246 issued to Mullane, et al. on Apr. 13, 1982; U.S. Pat. No. 4,342,314 issued to Radel. et al. on Aug. 3, 1982; U.S. Pat. No. 4,463,045 issued to Ahr et al. on Jul. 31, 1984; and U.S. Pat. No. 5,006,394 issued to Baird on Apr. 9, 1991. Each of these patents is incorporated herein by reference. Particularly preferred microapertured formed film topsheets are disclosed in U.S. Pat. No. 4,609,518 issued to Curro et al. on Sep. 2, 1986 and U.S. Pat. No. 4,629,643 issued to Curro et al. on Dec. 16, 1986, which are hereby incorporated by reference. The preferred topsheet for use in feminine hygiene products is the formed film described in one or more of the above patents and marketed on sanitary napkins by The Procter & Gamble Company of Cincinnati, Ohio as "DRI-WEAVE®."

The body facing surface of the formed film topsheet can be hydrophilic so as to help body liquids to transfer through the topsheet faster than if the body surface were not hydrophilic so as to diminish the likelihood that liquid will flow off the topsheet rather than flowing into and being absorbed by the absorbent structure. In a preferred embodiment, surfactant is incorporated into the polymeric materials of the formed film topsheet such as is described in U.S. Statutory Invention Registration No. H1670 to Aziz et al., published on Jul. 1, 1997, which is hereby incorporated by reference. Alternatively, the body facing surface of the topsheet can be made hydrophilic by treating it with a surfactant such as is described in U.S. Pat. No. 4,950,254, hereby incorporated by reference. In alternative embodiments (not shown) of the present invention, the absorbent article may be provided with means for improving contact between the topsheet and a wearer's skin. In one embodiment, the absorbent article can be provided with elastic means, as described in U.S. Pat. No. 4,892,536 issued in the name of DesMarais, et al. on Jan. 9, 1990, in U.S. Pat. No. 4,990,147, issued in the name of Freeland on Feb. 5, 1991, and in U.S. patent application Ser. No. 07/993,198, filed in the name of Freeland, et al. on Dec. 18, 1992 now U.S. Pat. No. 6,010,490, which lift the topsheet to improve contact with a wearer's perianal region. In another embodiment, described in U.S. Pat. No. 5,171,236, issued in the name of Drier, et al. on Dec. 15, 1992, a diaper is provided with spacing means to lift the topsheet. In yet another embodiment, described in U.S. Statutory Invention Registration H1687, published in the name of Roe, et al. on Oct. 7, 1997, the absorbent article is provided with a gluteal blocking device which lifts the topsheet into a wearer's gluteal groove.

In a preferred embodiment of a diaper as described herein, the backsheet 530 has a modified hourglass shape extending beyond the absorbent core a minimum distance of about 1.3 cm to about 6.4 cm (about 0.5 to about 2.5 inch) around the entire diaper periphery.

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent materials for use as the absorbent core of articles useful in the present methods are described, e.g., in U.S. Pat. No. 4,610,678 issued to Weisman et al. on Sep. 9, 1986; U.S. Pat. No. 4,673,402 issued to Weisman et al. on Jun. 16, 1987; U.S. Pat. No. 4,888,231 issued to Angstadt on Dec. 19, 1989; and U.S. Pat. No. 4,834,735 issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423 issued to Alemany et al., on Aug. 10, 1993; and in U.S. Pat. No. 5,147,345 issued to Young, LaVon and Taylor on Sep. 15, 1992. All of these patents are hereby incorporated by reference.

In a preferred embodiment, the diaper 50 further comprises elasticized leg cuffs 550 for providing improved containment of liquids and other body exudates; an elastic waist feature 560 that provides improved fit and containment; and a fastening system 570 which forms a side closure which maintains the first waist region 56 and the second waist region 58 in an overlapping configuration such that lateral tensions are maintained around the circumference of the diaper to maintain the diaper on the wearer. The diaper 50 may also comprise elasticized waist bands (not shown) and/or elasticized side panels (also not shown) in the waist regions 56 and 58 to provide an elastically extensible feature that provides a more comfortable and contouring fit and more effective application of the diaper 50.

The elasticized leg cuffs 550 can be constructed in a number of different configurations, including those described in U.S. Pat. No. 3,860,003; U.S. Pat. No. 4,909,803 issued to Aziz et al. on Mar. 20, 1990; U.S. Pat. No. 4,695,278 issued to Lawson on Sep. 22, 1987; and U.S. Pat. No. 4,795,454 issued to Dragoo on Jan. 3, 1989, the disclosure of each of which is hereby incorporated by reference. Absorbent articles having elasticized cuffs that are treated with a composition that may be useful herein are disclosed in co-pending U.S. patent application Ser. No., 08/766,386 now U.S. Pat. No. 6,156,024 and Ser. No. 08/840,039, now abandoned filed Dec. 3, 1996 and Apr. 24, 1997, respectively, the disclosures of both of which are hereby incorporated by reference.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, the disclosures of each of these references being hereby incorporated by reference.

The elasticized side panels may be constructed in a number of configurations. Examples of diapers with elasticized side panels positioned in the ears (ear flaps) of the diaper are disclosed in U.S. Pat. No. 4,857,067 issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and U.S. Pat. No. 5,151,092 issued to Buell et al. on Sep. 29, 1992; the disclosures of each of which are hereby incorporated by reference.

Exemplary fastening systems 570 are disclosed in U.S. Pat. No. 4,846,815 issued to Scripps on Jul. 11, 1989; U.S. Pat. No. 4,894,060 issued to Nestegard on Jan. 16, 1990; U.S. Pat. No. 4,946,527 issued to Battrell on Aug. 7, 1990; U.S. Pat. No. 3,848,594 issued to Buell on Nov. 19, 1974; U.S. Pat. No. 4,662,875 issued to Hirotsu et al. on May 5, 1987; and U.S. Pat. No. 5,151,092 issued to Buell et al. on Sep. 29, 1992; the disclosures of each of which are hereby incorporated by reference.

The diaper 50 is preferably applied to a wearer by positioning one of the waist regions of the diaper, preferably the second waist region 58, under the wearer's back and drawing the remainder of the diaper between the wearer's legs so that the other waist region, preferably the first waist region 56, is positioned across the front of the wearer. The fastening system is then applied to effect a side closure.

Of course, it will be recognized that any absorbent article design may be utilized in the present invention to incorporate a enzyme inhibitor and/or a delivery system for delivering the inhibitor onto the skin of a wearer during wear of the article, as described below. The disclosure above is merely for illustrative purposes.

The present invention may also employ training pants as an absorbent article comprising a enzyme inhibitor. The term "training pants", as used herein, refers to disposable garments having fixed sides and leg openings designed for infant or adults wearers. Training pants (also referred in the art as "pull on" products) are placed in position on the wearer by inserting the wearer's legs into the leg openings and sliding the training pant into position about the wearer's lower torso. Suitable training pants are disclosed in U.S. Pat. No. 5,246,433 issued to Hasse, et al. on Sep. 21, 1993, U.S. Pat. No. 5,569,234 issued to Buell et al. on Oct. 29, 1996, U.S. Pat. No. 4,940,464 issued to Van Gompel et al. on Jul. 10, 1990 and U.S. Pat. No. 5,092,861 issued to Nomura et al. on Mar. 3, 1992, the disclosures of each of which are hereby incorporated by reference.

Another disposable absorbent article for use in the present invention is an incontinence article. The term "incontinence article" refers to pads, undergarments (pads held in place by a suspension system of same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 issued to Buell; the above-mentioned U.S. Pat. No. 4,704,115; U.S. Pat. No. 4,909,802 issued to Ahr, et al.; U.S. Pat. No. 4,964,860 issued to Gipson, et al. on Oct. 23, 1990; and in U.S. Pat. No. 5,304,161 issued to Noel, et al. on Apr. 19, 1994. The disclosures of each of these references are hereby incorporated by reference.

Another disposable absorbent article for use in the present invention is a feminine hygiene article, such as a sanitary napkin. Suitable feminine hygiene articles are disclosed in U.S. Pat. No. 4,556,146 issued to Swanson et al. on Dec. 3, 1985; U.S. Pat. No. 4,589,876 issued to Van Tilberg on Apr. 27, 1993; U.S. Pat. No. 4,687,478 issued to Van Tilburg on Aug. 18, 1997; U.S. Pat. No. 4,950,264 issued to Osborn, III on Aug. 21, 1990; U.S. Pat. No. 5,009,653 issued to Osborn, III on Apr. 23, 1991; U.S. Pat. No. 5,267,992 issued to Van Tilburg on Dec. 7, 1993; U.S. Pat. No. 5,389,094 issued to Lavash et al. on Feb. 14, 1995; U.S. Pat. No. 5,413,568 issued to Roach et al. on May 9, 1995; U.S. Pat. No. 5,460,623 issued to Emenaker et al. on Oct. 24, 1995; U.S. Pat. No. 5,489,283 issued to Van Tilburg on Feb. 6, 1996; U.S. Pat. No. 5,569,231 issued to Emenaker et al. on Oct. 29, 1996; and U.S. Pat. No. 5,620,430 issued to Bamber on Apr. 15, 1997, the disclosures of each of which are hereby incorporated by reference.

IV. Enzyme Inhibition Assays

Standard in vitro assays for enzyme activity, and inhibition of enzyme activity, are well known. The reagents used to conduct these tests are generally commercially available. In general, a simple system comprises an enzyme-specific substrate which, when hydrolyzed by the enzyme, produces a colored product. The activity of the enzyme is measured spectrophotometrically as the degree of development of the colored product (i.e., the rate of color change) over a predetermined time period. Inhibition of enzyme activity is exhibited as a measurable decrease in the rate of color change over the same time period in the presence of an inhibitor. The following are exemplary methods that may be utilized to determine the inhibitory activity of enzyme inhibitors against A) purified enzymes known to exist in feces, B) specific enzyme activity in the feces itself and C) general enzyme activity in the feces itself. These methods are not intended to be limiting, however, as other methods, other substrates, other inhibitors and the like may be used to test activity against a wide variety of fecal enzymes, as known to one skilled in the art.

For each of the following exemplary Purified Enzyme Methods, Specific Fecal Enzyme Methods, General Fecal Enzymes Method, Purified Lipase activity assay, Fecal Lipase activity assay, Purified Urease activity assay, Fecal Urease activity assay, Purified Amylase activity assay, and Fecal Amylase activity assay, the IC50 for each inhibitor tested may be calculated according to the following equation:

$$IC_{50}=[I]/[(v/vi)-1],$$

where [I] is the inhibitor concentration tested, v is the rate of substrate cleavage in the absence of inhibitor and vi is the rate of substrate cleavage in the presence of inhibitor.

In the methods, v and vi are measured as the change in absorbance (optical density, OD) at a given wavelength/time (e.g., minutes).

A. Purified Enzyme Methods

1. Purified Trypsin Activity

To test the efficacy of protease inhibitors against purified trypsin, 0.05 mL of a putative inhibitor and 0.125 mL of 32 nM trypsin (e.g., Sigma, St. Louis, Mo., catalogue number T6424) in trypsin buffer (50 mM TRIS, 20 mM $CaCl_2$, pH 8.2) are added to a microcuvette. The cuvette is incubated at 25° C. for 10 minutes. To this mixture, 0.025 mL of substrate (4 mM Cbz-arginine-p-nitroanilide, e.g., Sigma, St. Louis, Mo., catalogue. no. C4893) in trypsin buffer is added to the cuvette, mixed, and the absorbance at 405 nm measured over 10 minutes at 25° C. The rate of substrate cleavage in the presence of inhibitor (vi) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, vi and v, and the inhibitor concentration [I] are used to calculate IC50 according to the equation expressed above.

2. Purified Chymotrypsin Activity

To test the efficacy of protease inhibitors against purified chymotrypsin, 0.05 mL of a putative inhibitor and 0.125 mL of 16 nM chymotrypsin (e.g., Sigma, St. Louis, Mo., catalogue no. C8946) in chymotrypsin buffer (50 mM TRIS, 10 mM $CaCl_2$, pH 7.6) are added to a microcuvette. The cuvette is incubated at 25° C. for 10 minutes. To this mixture, 0.025 mL of substrate (0.6 mM N-Succ-Ala-Ala-Pro-Phe-p-nitroanilide, e.g., Sigma cat. no. S7388) in chymotrypsin buffer is added to the cuvette, mixed, and the absorbance at 405 nm measured over 10 minutes at 25° C. The rate of substrate cleavage in the presence of inhibitor (vi) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, vi and v, and the inhibitor concentration [I] are used to calculate IC50 according to the equation expressed above.

3. Purified Leucine Aminopeptidase Activity

To test the efficacy of protease inhibitors against purified leucine aminopeptidase (LAP), 0.05 mL of a putative inhibitor and 0.125 mL of 0.06 U/mL LAP (e.g., Sigma, St. Louis, Mo., catalogue no. L5006) in LAP buffer (50 mM sodium phosphate, pH 7.2) are added to a microcuvette. The cuvette is incubated at 25° C. for 10 minutes. To this mixture, 0.025 mL of substrate (2.4 mM L-Leucine-p-nitroaniline, e.g., Sigma, St. Louis, Mo., catalogue no. L9125) in LAP buffer is added to the cuvette, mixed, and the absorbance at 405 nm measured over 10 minutes at 25° C. The rate of substrate cleavage in the presence of inhibitor (vi) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, vi and v, and the inhibitor concentration [I] are used to calculate IC50 according to the equation expressed above.

B. Specific Fecal Enzyme Methods

The following is a general description of a method for obtaining a sample of feces suitable for use in Fecal Protease Methods. However, one skilled in the art will be able to adapt the method to obtain appropriate samples of feces suitable for use in any of the Specific Fecal Protease Methods listed below (i.e., lipase, urease, and amylase) without undue experimentation.

For purposes of establishing a positive control to ensure that the pooled sample feces exhibit the requisite enzyme activity for assessing protease inhibitory activity, the following procedure is followed for each of the Fecal Protease Methods. Pooled infant feces (at least five different samples) are collected in a manner to keep them free of urine and contamination and mixed with water to obtain a weight by weight (w/w) mixture (e.g., 1:50 w/w). This mixture is then mixed thoroughly to obtain a homogeneous suspension by homogenization or sonication. The pooled fecal suspension is used as a source of protease activity as described below and will exhibit a rate of substrate turnover in the absence of inhibitor in the range of 0.005 OD405 per minute to 0.020 OD405 per minute. (Also, to ensure complete linearity the final absorbance should never exceed 1.5 OD405 units). If the activity of the pooled infant feces is outside this range, it is not possible to accurately determine IC50 values for putative protease inhibitors. However, the range of enzyme activity may be adjusted by increasing or decreasing the dilution factor accordingly for each enzyme. If this is not possible, a different group of subjects should be used to obtain the sample pool.

1. Fecal Trypsin Activity

To test the efficacy of protease inhibitors against the trypsin activity in feces, inhibitor and trypsin buffer (50 mM TRIS, 20 mM $CaCl_2$, pH 8.2) are added in a cuvette to obtain a final volume of 0.8 mL. To this mixture, 0.1 mL of substrate (3 mM Cbz-arginine-p-nitroanilide) is added to the cuvette. The cuvette is mixed by inversion and incubated at 25° C. for 5 minutes. A volume of 0.1 mL of fecal suspension is added to the cuvette, mixed and the absorbance at 405 nm minus the absorbance at 490 nm are measured over 5 minutes at 25° C. (The absorbance at 490 nm is a correction factor for the background absorbance due to the particulate fecal material, i.e., "interference"). The rate of substrate cleavage in the presence of inhibitor (vi) is the slope of a plot relating the excess absorbance (i.e., the absorbance at 405 nm minus the absorbance at 490 nm) versus time. The same procedure is repeated without the putative inhibitor. The rate of substrate cleavage in the absence of inhibitor (v) is the slope of a plot relating the excess absorbance versus time. The rates, vi and v, and the inhibitor concentration [I] are used to calculate IC50 according to the equation expressed above.

2. Fecal Chymotrypsin Activity

To test the efficacy of protease inhibitors against chymotrypsin activity in feces, inhibitor and chymotrypsin buffer (50 mM TRIS, 10 mM CaCl2, pH 7.6) are added in a cuvette to obtain a final volume of 0.92 mL. To this mixture, 0.04 mL of substrate (1.25 mM N-Succ-Ala-Ala-Pro-Phe-p-nitroanilide) is added to the cuvette. The cuvette is mixed by inversion and incubated at 25° C. for 5 minutes. A volume of 0.04 mL of fecal suspension is added to the cuvette, mixed and the absorbance at 405 nm minus the absorbance at 490 nm measured over 5 minutes at 25° C. The rate of substrate cleavage in the presence of inhibitor (vi) is the slope of a plot relating the excess absorbance (i.e., the absorbance at 405 nm minus the absorbance at 490 nm) versus time. The same procedure is repeated without the putative inhibitor. The rate of substrate cleavage in the absence of inhibitor (v) is the slope of a plot relating the excess absorbance versus time. The rates, vi and v, and the inhibitor concentration [I] are used to calculate IC50 according to the equation expressed above.

3. Fecal LAP Activity

To test the efficacy of protease inhibitors against LAP activity in feces, inhibitor and LAP buffer (50 mM sodium phosphate, pH 7.2) are added in a cuvette to obtain a final volume of 0.95 mL. To this mixture, 0.03 mL of substrate (6 mM L-Leucine-p-nitroanilide) is added to the cuvette. The cuvette is mixed by inversion and incubated at 25° C. for 5 minutes. A volume of 0.02 mL of fecal suspension is added to the cuvette, mixed and the absorbance at 405 nm minus the absorbance at 490 nm measured over 5 minutes at 25° C. The rate of substrate cleavage in the presence of inhibitor (vi) is the slope of a plot relating the excess absorbance (i.e., the absorbance at 405 nm minus the absorbance at 490 nm) versus time. The same procedure is repeated without the putative inhibitor. The rate of substrate cleavage in the absence of inhibitor (v) is the slope of a plot relating the excess absorbance versus time. The rates, vi and v, and the inhibitor concentration [I] are used to calculate IC50 according to the equation expressed above.

Using the Purified Protease and Fecal Protease assays described above, the protease inhibitory activity of exemplary protease inhibitors employed in the absorbent articles of the invention was tested and the results of the testing are illustrated in Table 1.

TABLE 1

| | IC50 ($\mu$M) | | | | | |
| --- | --- | --- | --- | --- | --- | --- |
| | Purified Enzyme Methods | | | Specific Fecal Enzyme Methods | | |
| Inhibitor | Trypsin | Chymotryp. | LAP* | Trypsin | Chymotryp. | LAP* |
| Soybean trypsin inhibitor | 0.25 | 0.026 | >10 | <0.01 | 0.06 | >20 |
| Aprotinin | 0.168 | 1 | >20 | 0.01 | 0.22 | >20 |
| Hexamidine diisethionate | 2.5 | >1000 | 256 | 2.3 | >1000 | 130 |
| p-Amino-benzamidine | 13.8 | >500 | >500 | 20 | >500 | >500 |
| Leupeptin | 0.14 | >500 | >500 | 0.11 | >500 | >500 |
| Pepstatin A | 324 | 4.9 | >500 | >500 | 300 | >500 |
| Chymostatin | >500 | <0.12 | >500 | >500 | 0.02 | >500 |
| TLCK** | 78.3 | >500 | >500 | 200 | >500 | >500 |
| Glycyrrhizic Acid | 45 | >500 | >500 | >300 | >300 | >300 |
| EDTA*** | >125,000 | >125,000 | >125,000 | 100 | 100 | >3000 |
| 4-(2-aminoethyl)-benzenesulfonylfluoride hydrochloride | 45.7 | 190 | >500 | — | — | — |

*LAP = leucine aminopeptidase

TABLE 1-continued

| | IC50 (µM) | | | | | |
|---|---|---|---|---|---|---|
| | Purified Enzyme Methods | | | Specific Fecal Enzyme Methods | | |
| Inhibitor | Trypsin | Chymotryp. | LAP* | Trypsin | Chymotryp. | LAP* |

**TLCK = L-1-chloro-3-[4-tosylamido]-7-amino-2-heptanone-HCl
***EDTA = ethylenediamine tetraacetic acid As illustrated in Table 1, each of the exemplary compounds inhibits at least one of the proteases tested by the Purified Enzyme and/or the Specific Fecal Enzyme methods employed.

C. General Fecal Enzymes Method

The general method described above for obtaining a sample of feces suitable for use in Specific Fecal Enzyme Methods can be easily adapted by one skilled in the art to obtain appropriate samples of feces suitable for use in the General Fecal Enzymes Method listed below without undue experimentation.

To test the efficacy of protease inhibitors against the protease activity in feces, 50 µL of inhibitor and 50 µL of fecal suspension are added to a 1.5 mL microcentrifuge tube. The microcentrifuge tube is mixed by inversion and incubated at 25° C. for 45 minutes. Then, 50 µL of protease buffer (200 mM TRIS buffer containing 20 mM CaCl$_2$, pH 7.8) is added to the microcentrifuge tube. The microcentrifuge tube is again mixed by inversion and incubated at 25° C. for 45 minutes. Then, 50 µL of protease substrate (0.4% casein-resorufin, e.g., Boehringer Mannheim, Indianapolis, Ind., catalogue no. 1,734,334) is added to the microcentrifuge tube. The microcentrifuge tube is again mixed by inversion and incubated at 37° C. for 60 minutes for the substrate cleavage reaction to take place. Then, 480 µL of trichloroacetic acid (5% w/v) is added to stop the reaction and precipitate any unreacted casein-resorufin. The microcentrifuge tube is mixed by inversion incubated at 37° C. for 15 minutes. The microcentrifuge tube is spun at a relative centrifugal force (RCF) of 20,800 times gravity for 5 min. Then, 400 µL of the supernatant is added to 600 µL of assay buffer (0.5 M TRIS, pH 8.8) in a cuvette. The cuvette is mixed by inversion and the absorbance at 574 nm are measured. The same procedure is repeated without the putative inhibitor. A is the absorbance at 574 nm in the absence of the inhibitor. Ai is the absorbance at 574 nm in the presence of the inhibitor. Before the start of the reaction, A and Ai are nearly zero. Therefore, the rate of substrate cleavage in the presence of inhibitor (vi) can be calculated by dividing the absorbance at 574 nm (Ai) over reaction time. The rate of substrate cleavage in the absence of inhibitor (v) can be calculated by dividing the absorbance at 574 nm (A) over reaction time. The rates, vi and v, and the inhibitor concentration [I] are used to calculate IC50 according to the equation expressed above.

TABLE 2

| Inhibitor | IC50 Values (µM) General Fecal Enzymes Method |
|---|---|
| Soybean trypsin inhibitor | 4.9 |
| Hexamidine | 31 |
| Leupetin | >320 |
| Pepstatin A | >32 |
| Chymostatin | 64 |

TABLE 2-continued

| Inhibitor | IC50 Values (µM) General Fecal Enzymes Method |
|---|---|
| 4-(2-aminoethyl)-benzenesulfonylfluoride hydrochloride | 217 |

D. Purified Lipase Activity

To test the efficacy of lipase inhibitors, 0.05 mL of a putative inhibitor and 0.125 mL of 160 nM pancreatic lipase (e.g., Sigma, St. Louis, Mo., catalogue number L0382) in 50 mM TRIS buffer containing 1 mM CaCl$_2$, pH 8.0, are added to a microcuvette. The cuvette is incubated at 25° C. for 10 minutes. To this mixture, 0.025 mL of substrate (1.25 mM p-nitrophenol caprylate, e.g., Sigma, St. Louis, Mo., catalogue no. N0752) is added to the cuvette and the mixture is incubated for an additional 5 minutes. The absorbance at 405 nm is then measured over 10 minutes at 25° C. The rate of substrate cleavage in the presence of inhibitor (vi) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, vi and v, and the inhibitor concentration [I] are used to calculate IC50 according to the equation expressed above.

E. Fecal Lipase Activity

To test the efficacy of lipase inhibitors against the lipase activity in feces, inhibitor and lipase buffer (50 mM TRIS buffer containing 1 mM CaCl$_2$, pH 8.0) are added to a cuvette to obtain a final volume of 0.8 mL. To this mixture, 0.1 mL of substrate (1.25 mM p-nitrophenol caprylate) is added to the cuvette. The cuvette is mixed by inversion and incubated at 25° C. for 5 minutes. A volume of 0.1 mL of fecal suspension is added to the cuvette, mixed and the absorbance at 405 nm minus the absorbance at 490 nm are measured over 5 minutes at 25° C. (The absorbance at 490 nm is a correction factor for the background absorbance due to the particulate fecal material, i.e., "interference".) The rate of substrate cleavage in the presence of inhibitor (vi) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, vi and v, and the inhibitor concentration [I] are used to calculate IC50 according to the equation expressed above.

F. Purified Urease Activity

To test the efficacy of urease inhibitors, 0.05 mL of a putative inhibitor and 0.125 mL of 0.08 U/mL Jack Bean urease (Sigma catalogue U2125) in 45 mM sodium phosphate buffer, pH 6.8, are added to a microcuvette. The cuvette is incubated at 25° C. for 10 minutes. To this mixture, 0.025 mL of substrate (300 mM urea, e.g., Sigma U0631) is added to the cuvette and the mixture is incubated for an additional 5 minutes. The liberation of ammonia is immediately determined using a commercially available ammonia detection kit (Sigma Diagnostics, St. Louis, Mo., Procedure 171).

G. Fecal Urease Activity

To test the efficacy of urease inhibitors against the urease activity in feces, inhibitor and urease buffer (45 mM sodium phosphate, pH 6.8) are added to a cuvette to obtain a final volume of 0.8 mL. To this mixture, 0.1 mL of substrate (375 mM urea) is added to the cuvette. The cuvette is mixed by inversion and incubated at 25° C. over 5 minutes. A volume of 0.1 mL of fecal suspension is added to the cuvette, mixed and incubated for an additional 5 minutes. The liberation of ammonia is immediately determined using a commercially available ammonia detection kit (Sigma Diagnostics, Procedure 171).

H. Purified Amylase Activity

Amylase activity is determined using Sigma Diagnostics Procedure 577. To test the efficacy of amylase inhibitors, 0.010 mL of a putative inhibitor and 0.010 mL of human salivary a-Amylase (Sigma # A0521; 100 to 2000 U/L, as measured by Sigma Diagnostics, Procedure 577) in water are added to a cuvette. The cuvette is incubated at 37° C. for 10 minutes. To this mixture, 1.00 mL of amylase substrate is added to the cuvette and the mixture is incubated for an additional 2 minutes. The absorbance at 405 nm is measured over 2 minutes at 37° C. The rate of substrate cleavage in the presence of inhibitor (vi) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, vi and v, and the inhibitor concentration [I] are used to calculate IC50 according to the equation expressed above.

I. Fecal Amylase Activity

Amylase activity is determined using Sigma Diagnostics Procedure 577. To test the efficacy of amylase inhibitors against the amylase activity in feces, 0.010 mL of a putative inhibitor and 0.010 mL of fecal suspension (100 to 2000 U/L, as measured by Sigma Diagnostics, Procedure 577) is added to a cuvette. The cuvette is incubated at 37° C. for 10 minutes. To this mixture, 1.00 mL of amylase substrate is added to the cuvette and the mixture is incubated for an additional 2 minutes. The absorbance at 405 nm minus the absorbance at 490 nm is measured over 2 minutes at 37° C. The rate of substrate cleavage in the presence of inhibitor (vi) is the slope of a plot relating the absorbance at 405 nm versus time. The same procedure is repeated without the putative inhibitor. The rate of substrate cleavage in the absence of inhibitor (v) is the slope of a plot relating the absorbance at 405 nm versus time. The rates, vi and v, and the inhibitor concentration [I] are used to calculate IC50 according to the equation expressed above.

V. Skin Care Compositions

Skin care compositions suitable for use in the absorbent articles of the invention are described in pending U.S. patent application Ser. Nos. 08/926,532 and 08/926,533, each filed on Sep. 10, 1997; U.S. Pat. No. 5,607,760, issued Mar. 4, 1997; U.S. Pat. No. 5,609,587, issued Mar. 11, 1997; U.S. Pat. No. 5,635,191, issued Jun. 3, 1997; and U.S. Pat. No. 5,643,588, issued Jul. 1, 1997, the disclosures of each of which are hereby incorporated by reference. As indicated, the skin care composition is transferred to the skin of a wearer of a treated article by normal contact, wearer motion and/or body heat. As such, transfer of the enzyme inhibitor-containing skin care composition begins upon application of the article to the wearer, and continues throughout the wear period. Thus, the enzyme inhibitor is generally present on the skin of the wearer prior to insult by body exudates.

In addition to its function as a vehicle for delivering a minimum inhibitor concentration of an enzyme inhibitor to a wearer's skin, the skin care composition that comprises the enzyme inhibitor also preferably comprises ingredients that, for example, reduce the adherence of feces to skin (e.g., to improve the ease of bowel movement clean up), provide a skin/feces barrier function (e.g., to coat the skin to prevent the adherence of feces) while remaining relatively liquid impervious but vapor pervious, or provide other therapeutic benefits to the skin (e.g., improve skin softness, maintain or improve skin health), and the like. The skin care composition may be in a variety of forms, including, but not limited to, emulsions, lotions, creams, ointments, salves, suspensions, encapsulations, gels, and the like.

In order to deliver an effective concentration of the enzyme inhibitor to the skin via an absorbent article over time, an effective amount of the skin care composition applied to or migrated to one or more of the wearer-contacting surfaces of the article depends, to a large extent, on the particular composition used. The quantity of the composition on at least a portion of the wearer-contacting surface of the absorbent article preferably ranges from about 0.05 mg/in$^2$ (0.0078 mg/cm$^2$) to about 80 mg/in$^2$ (12 mg/cm$^2$), more preferably from about 1 mg/in$^2$ (0.16 mg/cm$^2$) to about 40 mg/in$^2$ (6 mg/cm$^2$), still more preferably from about 4 mg/in$^2$ (0.6 mg/cm$^2$) to about 26 mg/in$^2$ (4 mg/cm$^2$). However, these ranges are by way of illustration only and the skilled artisan will recognize that the nature of the composition will dictate the level that must be applied to deliver an effective concentration of the enzyme inhibitor and that the desirable level is ascertainable by routine experimentation in light of the present disclosure.

While the amount of skin care composition applied to the absorbent article is an important aspect of the present invention, more important is the amount of composition transferred to the wearer's skin during use of one or more treated articles. Though the amount of the enzyme inhibitor-containing composition delivered to the skin will depend to some degree on the nature of the composition employed and the potency of the enzyme inhibitor, relatively low amounts may be delivered while still providing a minimum inhibitory concentration of the enzyme inhibitor to the skin. This is particularly true for preferred compositions, such as that described in Example 1.

With regard to the level of skin care composition that is transferred to the wearer during use of one treated absorbent article worn for a period of about 3 hours (a typical daytime wear time), particularly for preferred skin care compositions such as that described in Example 1, preferred is where at least about 0.01 mg/in$^2$ (0.0016 mg/cm$^2$), more preferably at least about 0.05 mg/in$^2$ (0.0078 mg/cm$^2$), still more preferably at least about 0.1 mg/in$^2$ (0.016 mg/cm$^2$), of the composition is transferred to the skin over a three hour wear period. Typically, the amount of composition delivered by one treated article will be from about 0.01 mg/in$^2$ (0.0016 mg/cm$^2$) to about 5 mg/in$^2$ (0.78 mg/cm$^2$), more preferably from about 0.05 mg/in$^2$ (0.0078 mg/cm$^2$) to about 3 mg/in$^2$ (0.47 mg/cm$^2$), still more preferably from about 0.1 mg/in$^2$ (0.016 mg/cm$^2$) to about 2 mg/in$^2$ (0.31 mg/cm$^2$), over a three hour wear period.

For continual use of treated articles (in other words, changes occur in accordance with normal use patterns, which typically include changes every 3 to 4 hours during the day and a fresh article before overnight sleep) such as for a period of 24 hours, it will be preferred that at least about 0.03 mg/in$^2$ (0.0047 mg/cm$^2$), more preferably at least about 0.1 mg/in$^2$ (0.016 mg/cm$^2$), still more preferably at least about 0.3 mg/in$^2$ (0.047 mg/cm$^2$), of the composition is transferred to the wearer's skin over the 24 hour period. Typically, the amount of composition delivered after a period of 24 hours where treated articles are applied at each change, will be from about 0.03 mg/in$^2$ (0.0047 mg/cm$^2$) to about 18 mg/in$^2$ (2.79 mg/cm$^2$), more typically from about 0.1 mg/in$^2$ (0.016 mg/cm$^2$) to about 10 mg/in$^2$ (1.55 mg/cm$^2$), still more typically from about 0.3 mg/in$^2$ (0.047 mg/cm$^2$) to about 6 mg/in$^2$ (0.93 mg/cm$^2$). A method for determining the amount of the skin care composition transferred to the skin during wear of the treated article is described below.

It will be recognized that of the numerous materials useful in the enzyme inhibitor-containing skin care compositions delivered to skin in accordance with the invention, those that have been deemed safe and effective skin care agents are logical materials for use herein. Such materials include Category I actives as defined by the U.S. Food and Drug Administration's (FDA) Tentative Final Monograph on Skin Protectant Drug Products for Over-the-Counter Human Use (21 C.F.R. §347), which presently include: allantoin, aluminum hydroxide gel, calamine, cocoa butter, dimethicone, cod liver oil (in combination), glycerine, kaolin, petrolatum, lanolin, mineral oil, shark liver oil, white petrolatum, talc, topical starch, zinc acetate, zinc carbonate, zinc oxide, and the like. Other potentially useful materials are Category III actives as defined by the U.S. Food and Drug Administration's Tentative Final Monograph on Skin Protectant Drug Products for Over-the-Counter Human Use (21 C.F.R. §347), which presently include: live yeast cell derivatives, aldioxa, aluminum acetate, microporous cellulose, cholecalciferol, colloidal oatmeal, cysteine hydrochloride, dexpanthenol, Peruvean balsam oil, protein hydrolysates, racemic methionine, sodium bicarbonate, Vitamin A, and the like.

Many of the FDA monographed skin care ingredients are currently utilized in commercially available skin care products, such as A and D® Ointment, Vaseline® Petroleum Jelly, Desitin® Diaper Rash Ointment and Daily Care® ointment, Gold Bond® Medicated Baby Powder, Aquaphor® Healing Ointment, Baby Magic® Baby Lotion, Johnson's Ultra Sensitive® Baby Cream. An effective concentration of an enzyme inhibitor may be incorporated into any of these commercial products and applied to absorbent articles to create treated articles for use in the present invention.

As discussed further hereinafter, the skin care compositions useful for transferring enzyme inhibitors to the skin of the wearer preferably, though not necessarily, have a melting profile such that they are relatively immobile and localized on the wearer-contacting surface of the article at room temperature, are readily transferable to the wearer at body temperature, and yet are not completely liquid under extreme storage conditions. In this regard, the compositions are at least partially transferable to the skin by way of normal contact, wearer motion, and/or body heat. Because the composition preferably is substantially immobilized on the article's wearer-contacting surface, relatively low levels of composition are needed to impart the desired skin care benefits. In addition, special barrier or wrapping materials may be unnecessary in packaging the treated articles useful in the methods of the present invention.

In a preferred embodiment, the skin care compositions useful herein are water-in-oil emulsions, wherein the enzyme inhibitor is in the aqueous phase. However, the skin care composition itself may be solid or more often semi-solid, at 20° C., i.e., at ambient temperatures. By "semisolid" is meant that the composition has a rheology typical of pseudoplastic or plastic liquids. When no shear is applied, the compositions can have the appearance of a semi-solid but can be made to flow as the shear rate is increased. This is due to the fact that, while the composition contains primarily solid components, it also includes a liquid component. Preferably, the enzyme inhibitor-containing compositions of the present invention have a zero shear viscosity between about $1.0 \times 10^6$ centipoise and about $1.0 \times 10^8$. More preferably, the zero shear viscosity is between about $5.0 \times 10^6$ centipoise and about $5.0 \times 10^7$ centipoise. As used herein the term "zero shear viscosity" refers to a viscosity measured at very low shear rates (e.g., 1.0 sec$^{-1}$) using plate and cone viscometer (a suitable instrument is available from TA Instruments of New Castle, Del. as model number CSL 100). One of skill in the art will recognize means other than high melting point components (as discussed below) can be used to provide comparable viscosities measured for such compositions comprising such means can be measured by extrapolating a plot of viscosity vs. shear rate for such compositions to a shear rate of zero at a temperature of about 20° C.

Preferred compositions are at least semi-solid at room temperature to minimize composition migration into the absorbent article before use. In addition, the compositions preferably have a final melting point (100% liquid) above potential "stressful" storage conditions that can be greater than 45° C. (e.g., warehouse in Arizona, car trunk in Florida, etc.). Representative compositions having these melt characteristics are described in detail in U.S. Pat. Nos. 5,643,588, 5,607,760, 5,609,587, and 5,635,191, the disclosure of each of which has been incorporated herein by reference. Specifically, preferred compositions will have the following melt profile:

| Characteristic | Preferred Range | Most Preferred |
| --- | --- | --- |
| % liquid at room temp. (20° C.) | 2–50 | 3–25 |
| % liquid at body temp. (37° C.) | 25–95 | 30–90 |
| final melting point (° C.) | ≧38 | ≧45 |

By being solid or semisolid at ambient temperatures, preferred compositions containing the enzyme inhibitors do not have a tendency to flow and migrate to a significant degree to undesired locations of the article to which they are applied. This means less skin care composition is required for imparting desirable therapeutic, protective and/or conditioning benefits.

To enhance immobility of preferred compositions, the viscosity of the formulated compositions should be as high as possible to prevent flow within the article to undesired location. Unfortunately, in some instances, higher viscosities may inhibit transfer of composition to the wearer's skin. Therefore, a balance should be achieved so the viscosities are high enough to keep the compositions localized on the surface of the article, but not so high as to impede transfer to the wearer's skin. Suitable viscosities for the compositions will typically range from about 5 to about 500 centipoise, preferably from about 5 to about 300 centipoise, more preferably from about 5 to about 100 centipoise, measured at 60° C. using a rotational viscometer (a suitable viscometer is available from Lab Line Instruments, Inc. of Melrose Park, Ill. as Model 4537). The viscometer is operated at 60 rpm using a number 2 spindle.

For skin care compositions designed to provide a therapeutic and/or skin protective benefit in addition to the benefit derived from the enzyme inhibitor, a useful active ingredient in these compositions is one or more skin protectants or emollients. As used herein, the term "emollient" is a material that protects against wetness or irritation, softens, soothes, supples, coats, lubricates, moisturizes, protects and/or cleanses the skin. (It will be recognized that several of the monographed actives listed above are "emollients", as that term is used herein.) In a preferred embodiment, these emollients will have either a plastic or liquid consistency at ambient temperatures, i.e., 20° C.

Representative emollients useful in the present invention include, but are not limited to, emollients that are petroleum-based; sucrose ester fatty acids; polyethylene glycol and derivatives thereof; humectants; fatty acid ester type; alkyl ethoxylate type; fatty acid ester ethoxylates; fatty alcohol type; polysiloxane type; propylene glycol and derivatives thereof; glycerine and derivatives thereof, including glyceride, acetoglycerides, and ethoxylated glycerides of $C_{12}-C_{28}$ fatty acids; triethylene glycol and derivatives thereof; spermaceti or other waxes; fatty acids; fatty alcohol ethers, particularly those having from 12 to 28 carbon atoms in their fatty chain, such as stearic acid; propoxylated fatty alcohols; other fatty esters of polyhydroxy alcohols; lanolin and its derivatives; kaolin and its derivatives; any of the monographed skin care agents listed above; or mixtures of these emollients. Suitable petroleum-based emollients include those hydrocarbons, or mixtures of hydrocarbons, having chain lengths of from 16 to 32 carbon atoms. Petroleum based hydrocarbons having these chain lengths include mineral oil (also known as "liquid petrolatum") and petrolatum (also known as "mineral wax," "petroleum jelly" and "mineral jelly"). Mineral oil usually refers to less viscous mixtures of hydrocarbons having from 16 to 20 carbon atoms. Petrolatum usually refers to more viscous mixtures of hydrocarbons having from 16 to 32 carbon atoms. Petrolatum and mineral oil are particularly preferred emollients for compositions of the present invention.

Suitable fatty acid ester type emollients include those derived from $C_{12}-C_{28}$ fatty acids, preferably $C_{16}-C_{22}$ saturated fatty acids, and short chain ($C_1-C_8$, preferably $C_1-C_3$) monohydric alcohols. Representative examples of such esters include methyl palmitate, methyl stearate, isopropyl laurate, isopropyl myristate, isopropyl palmitate, ethylhexyl palmitate and mixtures thereof. Suitable fatty acid ester emollients can also be derived from esters of longer chain fatty alcohols ($C_{12}-C_{28}$, preferably $C_{12}-C_{16}$) and shorter chain fatty acids e.g., lactic acid, such as lauryl lactate and cetyl lactate.

Suitable alkyl ethoxylate type emollients include $C_{12}-C_{22}$ fatty alcohol ethoxylates having an average degree of ethoxylation of from about 2 to about 30. Preferably, the fatty alcohol ethoxylate emollient is selected from the group consisting of lauryl, cetyl, and stearyl ethoxylates, and mixtures thereof, having an average degree of ethoxylation ranging from about 2 to about 23. Representative examples of such alkyl ethoxylates include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) and steareth-10 (a stearyl alcohol ethoxylate having an average degree of ethoxylation of 10). When employed, these alkyl ethoxylate emollients are typically used in combination with the petroleum-based emollients, such as petrolatum, at a weight ratio of alkyl ethoxylate emollient to petroleum-based emollient of from about 1:1 to about 1:5, preferably from about 1:2 to about 1:4.

Suitable fatty alcohol type emollients include $C_{12}-C_{22}$ fatty alcohols, preferably $C_{16}-C_{18}$ fatty alcohols. Representative examples include cetyl alcohol and stearyl alcohol, and mixtures thereof. When employed, these fatty alcohol emollients are typically used in combination with the petroleum-based emollients, such as petrolatum, at a weight ratio of fatty alcohol emollient to petroleum-based emollient of from about 1:1 to about 1:5, preferably from about 1:1 to about 1:2.

Other suitable types of emollients for use herein include polysiloxane compounds. In general, suitable polysiloxane materials for use in the present invention include those having monomeric siloxane units of the following structure:

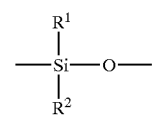

wherein, $R^1$ and $R^2$, for each independent siloxane monomeric unit can each independently be hydrogen or any alkyl, aryl, alkenyl, alkaryl, arakyl, cycloalkyl, halogenated hydrocarbon, or other radical. Any of such radicals can be substituted or unsubstituted. $R^1$ and $R^2$ radicals of any particular monomeric unit may differ from the corresponding functionalities of the next adjoining monomeric unit. Additionally, the polysiloxane can be either a straight chain, a branched chain or have a cyclic structure. The radicals $R^1$ and $R^2$ can additionally independently be other silaceous functionalities such as, but not limited to siloxanes, polysiloxanes, silanes, and polysilanes. The radicals $R^1$ and $R^2$ may contain any of a variety of organic functionalities including, for example, alcohol, carboxylic acid, phenyl, and amine functionalities.

Exemplary alkyl radicals are methyl, ethyl, propyl, butyl, pentyl, hexyl, octyl, decyl, octadecyl, and the like. Exemplary alkenyl radicals are vinyl, allyl, and the like. Exemplary aryl radicals are phenyl, diphenyl, naphthyl, and the like. Exemplary alkaryl radicals are toyl, xylyl, ethylphenyl, and the like. Exemplary aralkyl radicals are benzyl, alpha-phenylethyl, beta-phenylethyl, alpha-phenylbutyl, and the like. Exemplary cycloalkyl radicals are cyclobutyl, cyclopentyl, cyclohexyl, and the like. Exemplary halogenated hydrocarbon radicals are chloromethyl, bromoethyl, tetrafluorethyl, fluorethyl, trifluorethyl, trifluorotloyl, hexafluoroxylyl, and the like.

Viscosity of polysiloxanes useful may vary as widely as the viscosity of polysiloxanes in general vary, so long as the polysiloxane is flowable or can be made to be flowable for application to the absorbent article. This includes, but is not limited to, viscosity as low as 5 centistokes (at 37° C. as measured by a glass viscometer) to about 20,000,000 centistokes. Preferably the polysiloxanes have a viscosity at 37° C. ranging from about 5 to about 5,000 centistokes, more preferably from about 5 to about 2,000 centistokes, most preferably from about 100 to about 1000 centistokes. High viscosity polysiloxanes which themselves are resistant to flowing can be effectively deposited upon the absorbent articles by such methods as, for example, emulsifying the polysiloxane in surfactant or providing the polysiloxane in solution with the aid of a solvent, such as hexane, listed for exemplary purposes only. Particular methods for applying polysiloxane emollients to absorbent articles are discussed in more detail hereinafter.

Preferred polysiloxanes compounds for use in the present invention are disclosed in U.S. Pat. No. 5,059,282

(Ampulski et al), issued Oct. 22, 1991, which is incorporated herein by reference. Particularly preferred polysiloxane compounds for use as emollients in the compositions of the present invention include phenyl-functional polymethylsiloxane compounds (e.g., Dow Corning 556 Cosmetic-Grade Fluid: polyphenylmethylsiloxane) and cetyl or stearyl functionalized dimethicones such as Dow 2502 and Dow 2503 polysiloxane liquids, respectively. In addition to such substitution with phenyl-functional or alkyl groups, effective substitution may be made with amino, carboxyl, hydroxyl, ether, polyether, aldehyde, ketone, amide, ester, and thiol groups. Of these effective substituent groups, the family of groups comprising phenyl, amino, alkyl, carboxyl, and hydroxyl groups are more preferred than the others; and phenyl-functional groups are most preferred.

Suitable fatty ester type emollients also include polyolpolyesters as described in U.S. Pat. No. 5,609,587, issued to Roe on Mar. 11, 1997, the disclosure of which is incorporated herein by reference. Exemplary polyols include, but are not limited to, polyhydric compounds such as pentaerythritol; sugars such as raffinose, maltodextrose, galactose, sucrose, glucose, xylose, fructose, maltose, lactose, mannose and erythrose; and sugar alcohols such as erythritol, xylitol, malitol, mannitol and sorbitol. Such polyols are esterified with fatty acids and/or other organic radicals having at least two carbon atoms and up to 30 carbon atoms. While it is not necessary that all of the hydroxyl groups of the polyol be esterified, preferred polyolpolyester emollients of the present invention have substantially all (e.g., at least about 85%) of the hydroxyl groups esterified. Particularly preferred are sucrose polyolpolyesters such as sucrose polycottonate, sucrose polysoyate, and sucrose polybehenate. Mixtures of such polyolpolyesters are also suitable emollients for the present invention.

Suitable humectants include glycerine, propylene glycol, sorbitol, trihydroxy stearin, and the like.

When present, the amount of emollient that can be included in the composition will depend on a variety of factors, including the particular emollient involved, the skin benefits desired, the other components in the composition and like factors. The composition will comprise from 0 to about 100%, by total weight, of the emollient. Preferably, the composition will comprise from about 10 to about 95%, more preferably from about 20 to about 80%, and most preferably from about 40 to about 75%, by weight, of the emollient.

Another optional, preferred component of the enzyme inhibitor-containing skin compositions useful in the present invention is an agent capable of immobilizing the composition (including the enzyme inhibitor, the preferred emollient and/or other skin condition/protective agents) in the desired location in or on the treated article. Because certain of the preferred components in the composition are of a plastic or liquid consistency at 20° C., they will tend to flow or migrate, even when subjected to modest shear. When applied to a wearer-contacting surface or other location of an absorbent article, especially in a melted or molten state, such components will not remain primarily in or on the treated region. Instead, they will tend to migrate and flow to undesired regions of the article.

Specifically, if any component in the skin care composition migrates into the interior of the article, it can cause undesired effects on the absorbency of the article core due to the hydrophobic characteristics of, for example, the emollients and other skin conditioning agents used in the compositions useful in the articles of the present invention. It also means that more skin care composition has to be applied to the article to get the desired skin benefits. Increasing the level of the skin care composition not only increases the cost, but also exacerbates the undesirable effect on the absorbency of the article's core and undesired transfer of composition during processing/converting of the treated articles.

The immobilizing agent counteracts the tendency of the skin care composition components to migrate or flow by keeping them primarily localized on the surface or in the region of the article to which the composition is applied. This is believed to be due, in part, to the fact that the immobilizing agent raises the melting point and/or viscosity of the composition above that of the mobile components.

It is also advantageous to "lock" the immobilizing agent on the wearer contacting surface or the region of the article to which it is applied. This can be accomplished by using immobilizing agents which quickly set up (i.e., solidify) upon application to the article. In addition, outside cooling of the treated article via blowers, fans, cold rolls, etc. can speed up crystallization of the immobilizing agent.

The immobilizing agent will preferably have a melting profile that will provide a composition that is solid or semisolid at ambient temperature. In this regard, preferred immobilizing agents will have a melting point of at least about 35° C. This is so the immobilizing agent itself will not have a tendency to migrate or flow. Preferred immobilizing agents will have melting points of at least about 40° C. Typically, the immobilizing agent will have a melting point in the range of from about 50° to about 150° C.

When utilized, immobilizing agents useful herein can be selected from any of a number of agents, so long as the enzyme-inhibiting properties of the skin care composition provide the skin benefits described herein. It will be recognized that certain emollients or classes of emollients will also have melt characteristics such that they are suitable as immobilizing agents. Such materials may function as both emollients and immobilizing agents. Preferred immobilizing agents will comprise a member selected from the group consisting of $C_{14}$–$C_{22}$ fatty alcohols, $C_{12}$–$C_{22}$ fatty acids, and $C_{12}$–$C_{22}$ fatty alcohol ethoxylates having an average degree of ethoxylation ranging from 2 to about 30, and mixtures thereof. Preferred immobilizing agents include $C_{16}$–$C_{18}$ fatty alcohols, most preferably crystalline high melting materials selected from the group consisting of cetyl alcohol, stearyl alcohol, behenyl alcohol, and mixtures thereof. (The linear structure of these materials can speed up solidification on the treated absorbent article.) Mixtures of cetyl alcohol and stearyl alcohol are particularly preferred. Other preferred immobilizing agents include $C_{16}$–$C_{18}$ fatty acids, most preferably selected from the group consisting of palmitic acid, stearic acid, and mixtures thereof. Mixtures of palmitic acid and stearic acid are particularly preferred. Still other preferred immobilizing agents include $C_{16}$–$C_{18}$ fatty alcohol ethoxylates having an average degree of ethoxylation ranging from about 5 to about 20. Preferably, the fatty alcohols, fatty acids and fatty alcohols are linear. Importantly, these preferred immobilizing agents such as the $C_{16}$–$C_{18}$ fatty alcohols increase the rate of crystallization of the composition causing the composition to crystallize rapidly onto the surface of the substrate.

Other types of immobilizing agents that may be used herein include polyhydroxy fatty acid esters, polyhydroxy fatty acid amides, and mixtures thereof. Preferred esters and amides will have three or more free hydroxy groups on the polyhydroxy moiety and are typically nonionic in character. Because of the possible skin sensitivity of those using articles to which the composition is applied, these esters and amides should also be relatively mild and non-irritating to the skin.

Suitable polyhydroxy fatty acid esters for use in the present invention will have the formula:

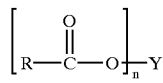

wherein R is a $C_5$–$C_{31}$ hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; Y is a polyhydroxyhydrocarbyl moiety having a hydrocarbyl chain with at least 2 free hydroxyls directly connected to the chain; and n is at least 1. Suitable Y groups can be derived from polyols such as glycerol, pentaerythritol; sugars such as raffinose, maltodextrose, galactose, sucrose, glucose, xylose, fructose, maltose, lactose, mannose and erythrose; sugar alcohols such as erythritol, xylitol, malitol, mannitol and sorbitol; and anhydrides of sugar alcohols such as sorbitan.

One class of suitable polyhydroxy fatty acid esters for use in the present invention comprises certain sorbitan esters, preferably the sorbitan esters of $C_{16}$–$C_{22}$ saturated fatty acids. Because of the manner in which they are typically manufactured, these sorbitan esters usually comprise mixtures of mono-, di-, tri-, etc. esters. Representative examples of suitable sorbitan esters include sorbitan palmitates (e.g., SPAN 40), sorbitan stearates (e.g., SPAN 60), and sorbitan behenates, that comprise one or more of the mono-, di- and tri-ester versions of these sorbitan esters, e.g., sorbitan mono-, di- and tri-palmitate, sorbitan mono-, di- and tri-stearate, sorbitan mono-, di and tri-behenate, as well as mixed tallow fatty acid sorbitan mono-, di- and tri-esters. Mixtures of different sorbitan esters can also be used, such as sorbitan palmitates with sorbitan stearates. Particularly preferred sorbitan esters are the sorbitan stearates, typically as a mixture of mono-, di- and tri-esters (plus some tetraester) such as SPAN 60, and sorbitan stearates sold under the trade name GLYCOMUL-S by Lonza, Inc. Although these sorbitan esters typically contain mixtures of mono-, di- and tri-esters, plus some tetraester, the mono- and di-esters are usually the predominant species in these mixtures.

Another class of suitable polyhydroxy fatty acid esters for use in the present invention comprises certain glyceryl monoesters, preferably glyceryl monoesters of $C_{16}$–$C_{22}$ saturated fatty acids such as glyceryl monostearate, glyceryl monopalmitate, and glyceryl monobehenate. Again, like the sorbitan esters, glyceryl monoester mixtures will typically contain some di- and triester. However, such mixtures should contain predominantly the glyceryl monoester species to be useful in the present invention.

Another class of suitable polyhydroxy fatty acid esters for use in the present invention comprise certain sucrose fatty acid esters, preferably the $C_{12}$–$C_{22}$ saturated fatty acid esters of sucrose. Sucrose monoesters and diesters are particularly preferred and include sucrose mono- and di-stearate and sucrose mono- and di-laurate.

Suitable polyhydroxy fatty acid amides for use in the present invention will have the formula:

wherein $R^1$ is H, $C_1$–$C_4$ hydrocarbyl, 2-hydroxyethyl, 2-hydroxypropyl, methoxyethyl, methoxypropyl or a mixture thereof, preferably $C_1$–$C_4$ alkyl, methoxyethyl or methoxypropyl, more preferably $C_1$ or $C_2$ alkyl or methoxypropyl, most preferably $C_1$ alkyl (i.e., methyl) or methoxypropyl; and $R^2$ is a $C_5$–$C_3$, hydrocarbyl group, preferably straight chain $C_7$–$C_{19}$ alkyl or alkenyl, more preferably straight chain $C_9$–$C_{17}$ alkyl or alkenyl, most preferably straight chain $C_{11}$–$C_{17}$ alkyl or alkenyl, or mixture thereof; and Z is a polyhydroxyhydrocarbyl moiety having a linear hydrocarbyl chain with at least 3 hydroxyls directly connected to the chain. See U.S. Pat. No. 5,174,927 (Honsa), issued Dec. 29, 1992 (herein incorporated by reference) which discloses these polyhydroxy fatty acid amides, as well as their preparation.

The Z moiety preferably will be derived from a reducing sugar in a reductive amination reaction; most preferably glycityl. Suitable reducing sugars include glucose, fructose, maltose, lactose, galactose, mannose, and xylose. High dextrose corn syrup, high fructose corn syrup, and high maltose corn syrup can be utilized, as well as the individual sugars listed above. These corn syrups can yield mixtures of sugar components for the Z moiety.

The Z moiety preferably will be selected from the group consisting of —$CH_2$—$(CHOH)_n$—$CH_2OH$, —CH($CH_2OH$)—[$(CHOH)_{n-1}$]—$CH_2OH$, —$CH_2OH$—$CH_2$—$(CHOH)_2(CHOR3)$—$(CHOH)$—$CH_2OH$, where n is an integer from 3 to 5, and $R^3$ is H or a cyclic or aliphatic monosaccharide. Most preferred are the glycityls where n is 4, particularly —$CH_2$—$(CHOH)_4$—$CH_2OH$.

In the above formula, $R^1$ can be, for example, N-methyl, N-ethyl, N-propyl, N-isopropyl, N-butyl, N-2-hydroxyethyl, N-methoxypropyl or N-2-hydroxypropyl. $R^2$ can be selected to provide, for example, cocamides, stearamides, oleamides, lauramides, myristamides, capricamides, palmitamides, tallowamides, etc. The Z moiety can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

The most preferred polyhydroxy fatty acid amides have the general formula:

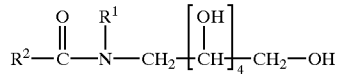

wherein $R^1$ is methyl or methoxypropyl; $R^2$ is a $C_1$–$C_{17}$ straight-chain alkyl or alkenyl group. These include N-lauryl-N-methyl glucamide, N-lauryl-N-methoxypropyl glucamide, N-cocoyl-N-methyl glucamide, N-cocoyl-N-methoxypropyl glucamide, N-palmityl-N-methoxypropyl glucamide, N-tallowyl-N-methyl glucamide, or N-tallowyl-N-methoxypropyl glucamide.

As previously noted, some of the immobilizing agents may require an emulsifier for solubilization in the emollient. This is particularly the case for certain of the glucamides such as the N-alkyl-N-methoxypropyl glucamides having HLB values of at least about 7. Suitable emulsifiers will typically include those having HLB values below about 7. In this regard, the sorbitan esters previously described, such as the sorbitan stearates, having HLB values of about 4.9 or less have been found useful in solubilizing these glucamide immobilizing agents in petrolatum. Other suitable emulsifiers include steareth-2 (polyethylene glycol ethers of stearyl alcohol that conform to the formula $CH_3(CH_2)_{17}(OCH_2CH_2)_nOH$, where n has an average value of 2), sorbitan tristearate, isosorbide laurate, and glyceryl monostearate. The emulsifier can be included in an amount sufficient to solubilize the immobilizing agent in the emollient such that a substantially homogeneous mixture is obtained. For example, an approximately 1:1 mixture of N-cocoyl-N-methyl glucamide and petrolatum that will normally not melt into a single phase mixture, will melt into a single phase mixture upon the addition of 20% of a 1:1 mixture of Steareth-2 and sorbitan tristearate as the emulsifier.

Other types of ingredients that can be used as immobilizing agents, either alone, or in combination with the above-mentioned immobilizing agents, include waxes such as camauba, ozokerite, beeswax, candelilla, paraffin, ceresin, esparto, ouricuri, rezowax, isoparaffin, and other known mined and mineral waxes. The high melt point of these materials can help immobilize the composition on the desired surface or location on the article. Additionally microcrystalline waxes are effective immobilizing agents. Microcrystalline waxes can aid in "locking" up low molecular weight hydrocarbons within the skin care composition. Preferably the wax is a paraffin wax. An example of a particularly preferred alternate immobilizing agent is a paraffin wax such as Parrafin S.P. 434 from Strahl and Pitsch Inc. P.O. Box 1098 West Babylon, N.Y. 11704.

The amount of the optional immobilizing agent that can be included in the composition will depend on a variety of factors, including the actives (e.g., emollients) involved, the particular immobilizing agent involved, if any, the other components in the composition, whether an emulsifier is required to solubilize the immobilizing agent in the other components, and like factors. When present, the composition will typically comprise from about 5 to about 90% of the immobilizing agent. Preferably, the composition will comprise from about 5 to about 50%, most preferably from about 10 to about 40%, of the immobilizing agent.

It is highly desirable that at least a portion of the article's topsheet be made of a hydrophilic material to promote rapid transfer of liquids (e.g., urine) through the topsheet. Similarly, it may be desirable that the composition be sufficiently wettable to ensure that liquids will transfer through the topsheet rapidly. Alternatively, hydrophobic skin care compositions may be utilized, so long as they are applied such that the fluid handling properties of the topsheet are adequately maintained. (For example, as discussed below, nonuniform application of the composition to the topsheet is one means to accomplish this goal.) This diminishes the likelihood that body exudates will flow off the composition-treated topsheet rather than being drawn through the topsheet and being absorbed by the absorbent core.

Where a hydrophilic composition is desired, depending upon the particular components used in the composition, a hydrophilic surfactant (or a mixture of hydrophilic surfactants) may, or may not, be required to improve wettability. For example, some immobilizing agents, such as N-cocoyl-N-methoxypropyl glucamide have HLB values of at least about 7 and are sufficiently wettable without the addition of hydrophilic surfactant. Other immobilizing agents such as the $C_{16}$–$C_{18}$ fatty alcohols having HLB values below about 7 may require addition of hydrophilic surfactant to improve wettability when the composition is applied to article topsheets. Similarly, a hydrophobic emollient such as petrolatum may require the addition of a hydrophilic surfactant if hydrophilic composition is desired. Of course, the concern around wettability is not a factor when the wearer-contacting surface under consideration is other than the article's topsheet or when fluid handling properties of the topsheet are adequately maintained via other means (e.g., nonuniform application).

Suitable hydrophilic surfactants will preferably be miscible with the other components of the skin care composition so as to form blended mixtures. Because of possible skin sensitivity of those using disposable absorbent products to which the composition is applied, these surfactants should also be relatively mild and non-irritating to the skin. Typically, these hydrophilic surfactants are nonionic to be not only non-irritating to the skin, but also to avoid other undesirable effects on any other structures within the treated article. For example, reductions in tissue laminate tensile strength, adhesive bond sufficiencies, and the like.

Suitable nonionic surfactants may be substantially nonmigratory after the composition is applied to the articles and will typically have HLB values in the range of from about 4 to about 20, preferably from about 7 to about 20. To be nonmigratory, these nonionic surfactants will typically have melt temperatures greater than the temperatures commonly encountered during storage, shipping, merchandising, and use of disposable absorbent products, e.g., at least about 30° C. In this regard, these nonionic surfactants will preferably have melting points similar to those of the immobilizing agents previously described.

Suitable nonionic surfactants for use in compositions that will be applied to the articles, at least in the liquid discharge region of the diaper, include alkylglycosides; alkylglycoside ethers as described in U.S. Pat. No. 4,011,389 (Langdon, et al), issued Mar. 8, 1977, which is incorporated by reference; alkylpolyethoxylated esters such as Pegosperse 1000MS (available from Lonza, Inc., Fair Lawn, N.J.), ethoxylated sorbitan mono-, di- and/or tri-esters of $C_{12}$–$C_{18}$ fatty acids having an average degree of ethoxylation of from about 2 to about 20, preferably from about 2 to about 10, such as TWEEN 60 (sorbitan esters of stearic acid having an average degree of ethoxylation of about 20) and TWEEN 61 (sorbitan esters of stearic acid having an average degree of ethoxylation of about 4), and the condensation products of aliphatic alcohols with from about 1 to about 54 moles of ethylene oxide. The alkyl chain of the aliphatic alcohol is typically in a straight chain (linear) configuration and contains from about 8 to about 22 carbon atoms. Particularly preferred are the condensation products of alcohols having an alkyl group containing from about 11 to about 22 carbon atoms with from about 2 to about 30 moles of ethylene oxide per mole of alcohol. Examples of such ethoxylated alcohols include the condensation products of myristyl alcohol with 7 moles of ethylene oxide per mole of alcohol, the condensation products of coconut alcohol (a mixture of fatty alcohols having alkyl chains varying in length from 10 to 14 carbon atoms) with about 6 moles of ethylene oxide. A number of suitable ethoxylated alcohols are commercially available, including TERGITOL 15-S-9 (the condensation product of $C_{11}$–$C_{15}$ linear alcohols with 9 moles of ethylene oxide), marketed by Union Carbide Corporation; KYRO EOB (condensation product of $C_{13}$–$C_{15}$ linear alcohols with 9 moles of ethylene oxide), marketed by The Procter & Gamble Co., the NEODOL brand name surfactants marketed by Shell Chemical Co., in particular NEODOL 25-12 (condensation product of $C_{12}$–$C_{15}$ linear alcohols with 12 moles of ethylene oxide) and NEODOL 23-6.5T (condensation product of $C_{12}$–$C_{13}$ linear alcohols with 6.5 moles of ethylene oxide that has been distilled (topped) to remove certain impurities), and especially the PLURAFAC brand name surfactants marketed by BASF Corp., in particular PLURAFAC A-38 (a condensation product of a $C_{18}$ straight chain alcohol with 27 moles of ethylene oxide). (Certain of the hydrophilic surfactants, in particular ethoxylated alcohols such as NEODOL 25-12, can also function as alkyl ethoxylate emollients). Other examples of preferred ethoxylated alcohol surfactants include ICI's class of Brij surfactants and mixtures thereof, with Brij 72 (i.e., Steareth-2) and Brij 76 (i.e., Steareth-10) being especially preferred. Also, mixtures of cetyl alcohol and stearyl alcohol ethoxylated to an average degree of ethoxylation of from about 10 to about 20 may also be used as the hydrophilic surfactant.

Another type of suitable surfactant for use in the composition includes Aerosol OT, a dioctyl ester of sodium sulfosuccinic acid marketed by American Cyanamid Company.

Still another type of suitable surfactant for use in the composition includes silicone copolymers such as General Electric SF 1188 (a copolymer of a polydimethylsiloxane and a polyoxyalkylene ether) and General Electric SF 1228 (a silicone polyether copolymer). These silicone surfactants can be used in combination with the other types of hydrophilic surfactants discussed above, such as the ethoxylated alcohols. These silicone surfactants have been found to be effective at concentrations as low as 0.1%, more preferably from about 0.25 to about 1.0%, by weight of the composition.

Where a hydrophilic composition is desired, the amount of hydrophilic surfactant required to increase the wettability of the composition to a desired level will depend in-part upon the HLB value and level of immobilizing agent, if any, used, the HLB value of the surfactant used and like factors. The composition can comprise from about 0.1 to about 50% of the hydrophilic surfactant when needed to increase the wettability properties of the composition. Preferably, the composition comprises from about 1 to about 25%, most preferably from about 10 to about 20%, of the hydrophilic surfactant when needed to increase wettability.

Compositions can comprise other components typically present in emulsions, creams, ointment, lotions, suspensions, etc. of this type. These components include water, viscosity modifiers, perfumes, disinfectant antibacterial actives, antiviral agents, vitamins, pharmaceutical actives, film formers, deodorants, opacifiers, astringents, solvents, preservatives, and the like. In addition, stabilizers can be added to enhance the shelf life of the composition such as cellulose derivatives, proteins and lecithin. All of these materials are well known in the art as additives for such formulations and can be employed in appropriate amounts in the compositions for use herein.

If water-based skin care compositions are used, a preservative will be needed. Suitable preservatives include propyl paraben, methyl paraben, benzyl alcohol, benzylkonnium, tribasic calcium phosphate, BHT, or acids such as citric, tartaric, maleic, lactic, malic, benzoic, salicylic, and the like. Suitable viscosity increasing agents include some of the agents described as effective immobilizing agents. Other suitable viscosity increasing agents include alkyl galactomannan, silica, talc, magnesium silicate, sorbitol, colloidal silicone dioxide, magnesium aluminum silicate, zinc stearate, wool wax alcohol, sorbiton, sesquioleate, cetyl hydroxy ethyl cellulose and other modified celluloses. Suitable solvents include propylene glycol, glycerine, cyclomethicone, polyethylene glycols, hexalene glycol, diol and multi-hydroxy based solvents. Suitable vitamins include A, D3, E, B5 and E acetate.

VI. Treating Articles with Composition

In preparing absorbent articles to carry out the methods of the present invention, the skin care composition containing the enzyme inhibitor is applied such that during wear, at least some portion of the composition will transfer from the treated article to the wearer's skin. That is, skin care composition is either applied directly to one or more wearer contacting surfaces, or is applied in alternate locations or means such that the skin care composition is readily available for transfer from one or more wearer contacting surfaces during use without intervention by the user/caregiver. (For example, materials positioned beneath the wearer contacting surface, encapsulated compositions, etc.) The skin care composition may be incorporated into any portion or portions of the article including, but not limited to, the topsheet, the backsheet, the absorbent core, any secondary layer(s) intermediate the core and the topsheet or the backsheet, a leg cuff, a side panel, a waist region, a fastener, an insertable element such as an absorbent material inserted into the absorbent article for use during wear of the article, a nanaophase structural elements, specialized structures such as those employed to contain bowel movements (e.g., bowel movement "pockets"), and the like.

Of course, to effectuate delivery of composition to those body regions most susceptible to skin roughness, it will be preferred to include the composition on the portion of the topsheet and cuffs that will contact the wearer's buttocks, genitals, intertriginous and anal regions during wear. Additionally, the composition may be applied to other article regions for delivery to one or more of the wearer's hips, abdomen, back, waist, sides, thighs, etc. Suitable methods include spraying, printing (e.g., flexographic printing), coating (e.g., contact slot coating, gravure coating), extrusion, or combinations of these application techniques, e.g., spraying the skin care composition on a rotating surface, such as a calender roll, that then transfers the composition to the desired portion of the article. The skin care composition containing the enzyme inhibitor can also be applied as a solid material via any of a variety methods, for example extrusion.

When applied to the article's topsheet, the manner of applying the composition to the article should be such that the topsheet does not become saturated with the composition, at least in the region corresponding to the liquid discharge region of the article, if the composition is hydrophobic in nature. If the topsheet becomes saturated with the composition in the liquid discharge region, there is a greater potential for the composition to block the topsheet openings, reducing the ability of the topsheet to transmit liquid to the underlying absorbent core. Also, saturation of the topsheet is not required to obtain the therapeutic and/or protective benefits. Similarly, saturation of other treated article components may not be necessary or desired to transfer sufficient composition for desired skin benefits. Particularly suitable application methods will apply the composition primarily to the outer surface of the topsheet of the article.

The minimum level of the composition containing the enzyme inhibitor to be applied to the article's wearer-contacting surface is an amount effective for providing the therapeutic, protective and/or skin conditioning benefits when the composition is delivered pursuant to the present invention. The level of composition applied will depend on various factors, including the article component treated, the relative amount of surface area of the wearer-contacting surface not treated with the composition, the composition's content and the like. In general, with compositions that are relatively hydrophobic and are to be applied to essentially all of the topsheet, the composition is preferably applied to the article topsheet in an amount ranging from about 0.1 mg/in$^2$ (0.016 mg/cm$^2$) to about 15 mg/in$^2$ (2.33 mg/cm$^2$), more preferably from about 1 mg/in$^2$ (0.16 mg/cm$^2$) to about 10 mg/in$^2$ (1.55 mg/cm$^2$). It will be recognized that higher levels of skin care composition may be applied to other article components where fluid handling properties are not impacted (e.g., cuffs, waist band, side panels, etc.). It will also be recognized that for compositions that are relatively hydrophilic, higher add-on levels may be used on the topsheet without adversely impacting liquid handling properties to an unacceptable degree. Conversely, higher levels of a hydrophilic composition may be undesired when applied to components (e.g., cuff, waist) other than the topsheet, to avoid wicking of exudates to the edges of the article which may result in leakage.

Because the composition is preferably substantially immobilized on the surface of the region treated, relatively small amounts of composition are needed to deliver an effective amount of the enzyme inhibitor. It is believed that the ability to use low levels to impart the desired skin benefits is due to the fact that the composition is continuously, automatically delivered as articles are worn. As indicated, the ability to use relatively low levels of skin care composition, allows the article's topsheet to maintain its liquid transfer properties in the liquid discharge region.

The composition can be applied nonuniformly to the wearer contacting surface of the article. By "nonuniform" it is meant that the amount, location, pattern of distribution, etc. of the composition can vary over the wearer-contacting surface, and may further vary over specific regions of the article. For example, to maintain the liquid handling performance of the topsheet, it may be desired to apply the composition nonuniformly to the topsheet, particularly if the composition is hydrophobic in nature. In this regard, some portions of the treated surface of the article (and regions thereof) can have greater or lesser amounts of composition, including portions of the surface that do not have any composition on it. When the composition is relatively hydrophobic, in one such preferred embodiment the surface of the topsheet will have regions where no composition is applied, particularly in areas of the topsheet that correspond to the crotch region of the article. As used herein, the crotch region of the article is the rectangle, defined below, that is centered longitudinally and laterally about the article's crotch point. The "crotch point" is determined by placing the article on a wearer in a standing position and then placing an extensible filament around the legs in a figure eight configuration. The point in the article corresponding to the point of intersection of the filament is deemed to be the crotch point of the article. (It is understood that the crotch point is determined by placing the absorbent article on a wearer in the intended manner and determining where the crossed filament would contact the article.) With regard to incontinence devices (e.g., diapers, adult incontinent articles), the length of the crotch region corresponds to 40% of the absorbent article's total length (i.e., in the y-dimension). With regard sanitary napkins, the length of the crotch region corresponds to 80% of the absorbent article's total length. The width of the crotch region is equivalent to the width of the widest absorbent core component as measured at the crotch point. (As used herein, "absorbent core" components are those materials involved with acquiring, transporting, distributing and/or storing body liquids. As such, the term absorbent core does not include the topsheet or backsheet of the absorbent article.) By way of illustration, for an incontinent article having a length of 20 in. and a core width at the crotch point of 4 in., the crotch region is the rectangle, centered on the crotch point, having a length of 8 in. and a width of 4 in.

Surprisingly, while the topsheet or other components comprising the composition are treated nonuniformly (e.g., microscopic or macroscopic regions where no composition is applied), during wear of the article, the composition is transferred to the wearer even in regions of the skin corresponding to untreated regions within the topsheet or other components. The amount and uniformity of composition transferred to the skin is believed to depend on several factors, including, for example, application pattern of the skin care composition, contact of the wearer's skin to the treated article surface, friction created during wear time between the wearer's skin and the treated region, warmth generated from wearer to enhance the transfer of the composition, the composition's properties, the materials which constitute the composition, and the like.

Where the composition is applied nonuniformly, any pattern may be utilized, including, for example, application of small droplets (obtained via, e.g., spraying) discrete dots (obtained via, e.g., gravure printing), stripes that run in the longitudinal or lateral direction of the article (obtained via contact slot coating), spirals that run in the longitudinal or lateral direction, etc., patterned prints, etc. In those embodiments where the topsheet comprises discrete, untreated regions, the percent open area of the region of the topsheet that corresponds to the crotch region of the article can vary widely. (As referred to herein, the "percent open area" of the topsheet is determined by (i) measuring the surface area of the topsheet that overlies the crotch region, (ii) measuring the total surface area of the untreated region(s) in this portion of the topsheet and (iii) dividing the measurement in (ii) by the measurement in (i). As used herein, "untreated" means a region of the topsheet having less than about 0.01 mg/in$^2$ (0.0016 mg/cm$^2$) of the composition. In this regard, the percent open area may be from about 1% to about 99%, from about 5% to about 95%, from about 10% to about 90%, from about 15% to about 85%, from about 20% to about 80%, from about 25% to about 75%, from about 30% to about 70%, or from about 35% to about 65%. The percent open area required to achieve the desired composition effect and the desired liquid handling properties of the topsheet will be dictated largely by the characteristics of the composition (in particular the composition's contents and its relative hydrophobicity/hydrophilicity properties). One skilled in the art will appreciate that the desired percent open area will be readily determined through routine experimentation.

In general, with compositions that are relatively hydrophobic and are to be applied such that regions of the topsheet are not coated with the composition, the composition is preferably applied to the article topsheet in an amount ranging from about 0.05 mg/in$^2$ (0.0078 mg/cm$^2$) to about 35 mg/in$^2$ (5.43 mg/cm$^2$), more preferably from about 1 mg/in$^2$ (0.16 mg/cm$^2$) to about 25 mg/in$^2$ (3.88 mg/cm$^2$), still more preferably 4 mg/in$^2$ (0.62 mg/cm$^2$) to about 20 mg/in$^2$ (3.1 mg/cm$^2$). It will be recognized that for compositions that are relatively hydrophilic, higher add-on levels may be used without adversely impacting liquid handling properties of the topsheet to an unacceptable degree. Of course, for articles having relatively high percent open areas in the crotch, greater add-on levels may be obtainable without adversely affecting liquid handling by the topsheet.

In one preferred embodiment for carrying out the present methods, the topsheet of the articles utilized will comprise stripes of composition that run in the article's longitudinal direction. These longitudinal stripes (or spirals) are separated by longitudinal stripes where little or no composition is applied to the topsheet. In these embodiments, each stripe of composition will typically have a width of from about 0.1 in. to about 0.75 in., more typically from about 0.1 in. to about 0.5 in., and the width of the stripes containing no composition will typically be from about 0.1 in. to about 1 in., more typically from about 0.15 to about 0.5 in. These ranges are applicable to typical infant diaper designs. For larger products such as adult incontinent products, these ranges may be higher.

Skin care composition can also be applied in nonuniform patterns on other article components. In these cases, the open area is calculated by the rectangle defined by the perimeters of the skin care composition.

The composition can be applied to the article at any point during assembly. For example, the composition can be applied to the finished disposable absorbent product before it has been packaged. The composition can also be applied to a given component (e.g., topsheet, cuffs, sides, waist, etc.), at the converting site or by the material supplier, before it is combined with the other raw materials to form a finished disposable absorbent product. Again, the composition can be applied to other zones of the article such that the composition will migrate to one or more wearer contacting surfaces during use.

The composition is typically applied from a melt thereof to the article. Since in a preferred embodiment, the composition melts at significantly above ambient temperatures, it is usually applied as a heated composition to the article. Typically, the composition is heated to a temperature in the range from about 35° to about 150° C., preferably from 40° to about 100° C., prior to being applied to the article. The enzyme inhibitor may be added to the composition prior to or after heating. If added prior to heating, the temperature to which the composition is heated is selected so as not to denature the enzyme inhibitor. Alternatively, the enzyme inhibitor may be added to the pre-heated composition when it has cooled to a temperature that does not affect the enzyme inhibitor but is still sufficiently liquid to be applied to the article. Once the melted composition has been applied to the article, it is allowed to cool and solidify.

Preferably, the application process is designed to aid in the cooling/set up of the composition.

In applying compositions to the articles, contact slot coating, spraying, gravure coating, extrusion coating methods are preferred. One such method involves slot coating of the composition on the article's topsheet after the topsheet is assembled with the other raw materials into a finished product.

VII. Test Methods

A. Transfer of Skin Care Composition and Enzyme Inhibitor to Wearer's Skin

Overview

This method uses a removable skin analog material that is placed on a wearer's skin for a controlled period of time. After the skin analog has been removed, it is extracted using an appropriate solvent and the amount of skin care composition or the amount of enzyme inhibitor deposited thereon is determined using known analytical methods. The method is described for use with infant diapers comprising skin care compositions containing enzyme inhibitors, as defined herein. One of skill in the art will recognize the appropriate changes for other skin care compositions, enzyme inhibitors, absorbent articles, or wearer types.

Subjects

Approximately equal numbers of male and female infants should be selected using the following inclusion and exclusion criteria. Sufficient infants should be selected to ensure that there are at least fifteen subjects per condition and transfer time who complete all aspects of the test.

Inclusion Criteria
a. Healthy infant
b. Caregiver willing to not use lotions, creams, powders or other skin preparations in the diaper area for the duration of the test.
c. Infants who wear disposable diapers full time.
d. Caregiver willing to give child bath the evening before the study and not again until after completion of the study.
e. Caregiver will to have child refrain from swimming from the evening before the study until after completion of the study.

Exclusion Criteria
a. The infant has been ill within the last four days.
b. Diarrhea (soft stool) any time during the four days before the test.
c. Medication which might increase frequency of bowel movements (e.g., oral antibiotics, anti fungal agents, corticosteroids).
d. Damaged skin in or around the test site (e.g., from sunburn, active dermal lesions, or the like).
e. Known allergies or irritation from adhesive or skin care ingredients.

Materials
In Vivo Transfer
Skin Analog: Dermatological Tape-TEGADERM Tape No. 1622W available from 3M Health Cares, St. Paul, Minn.
Sample Container: Glass jar with closure available from VWR Scientific, West Chester, Pa. as catalog Number 15900-242
Tape Release Powder: Baby powder (comprising only talc and fragrance) available from Johnson & Johnson, New Brunswick, N.J.
Surgical Gloves: Available from Best Manufacturing Co., Menlo Ga., as product 6005PFM.
Extraction and Analysis of Skin Care Composition
Extraction Solvent: Dichloromethane, available from Sigma-Aldrich of St. Louis, Mo. as 27056-3
Stearyl alcohol: Aldrich 25876-8
1-Hexadecanol: Aldrich 25874-1
Dispensing Flask: 10 ML
Gas Chromatograph: Flame ionization Detector, Hewlett Packard Model 5890 is suitable.
Column Capillary column: Chrompack CP Sil-5 CB, 2 meters X 0.25 mm id, 0.12 micron film thickness fused silica capillary (no substitutions)
Instrumental Data System: Must be able to reproducibly determine areas of peaks of interest.
Extraction and Analysis of an Exemplary Enzyme (e.g., Protease) Inhibitor (e.g., Hexamidine)
Extraction Solvent: Dichloromethane, available from Sigma-Aldrich of St. Louis, Mo. as 27056-3
Dispensing Flask: 10 mL
Column: Hewlett Packard Zorbax SB-CN narrow bore 5 micron, 2.1×150 mm with a Waters Bondapak CN 10 micron, 3.9×20 mm guard column.
Instrumental Data System: Must be able to reproducibly determine areas of peaks of interest.
Method
In Vivo Transfer
A. Confirm from the subject's caregiver that the subject has been bathed within the last 24 hours and that no lotions, powders, etc. have been applied to the diapered region of the subject's skin since bathing.

B. Wearing the surgical gloves, place the subject on the table and remove his/her diaper.

C. Turn the subject on his/her stomach.

D. Remove the release liner from a TEGADERM tape and lightly brush J&J Baby Powder over the adhesive surface (Wear surgical gloves, or the like, during application to prevent contamination of the tape). Provide sufficient powder such that there is a light coat of powder over all of the tape except the edges. (This step is done to keep the tape from adhering too aggressively to the child's skin.).

Figure 2:
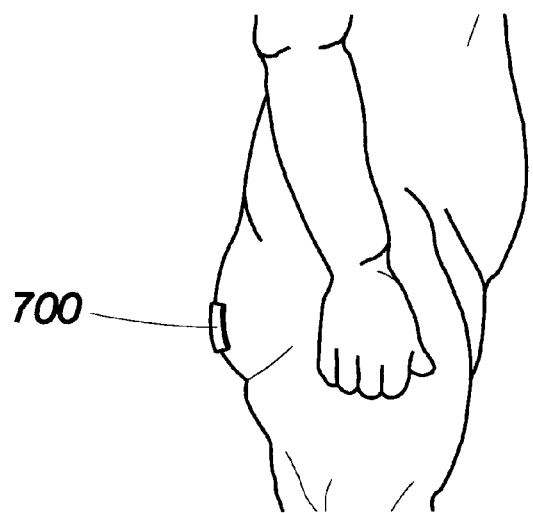
FIG. 2 is a side view showing placement of a skin analog used in the skin care composition transfer test and/or the enzyme inhibitor transfer test.
Figure 3:
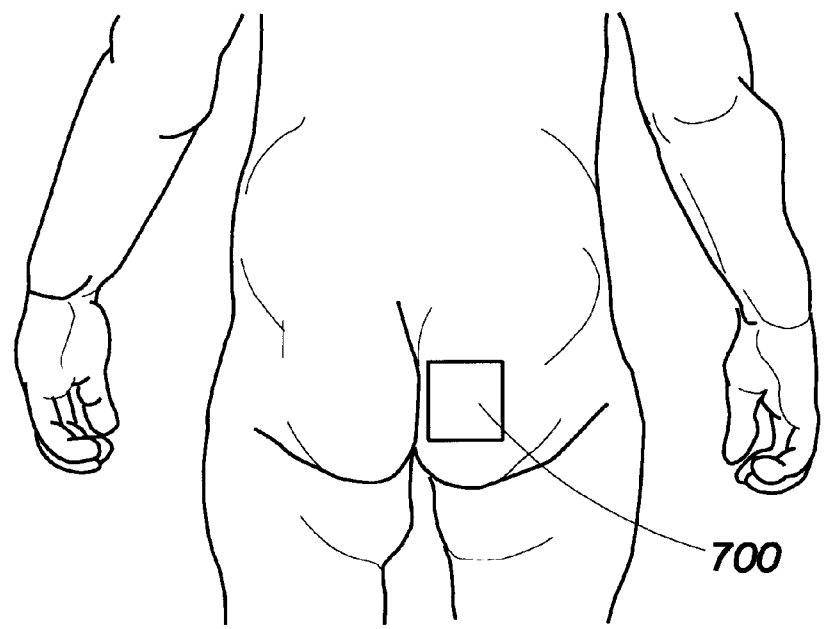
FIG. 3 is a plan view showing placement of the skin analog used in the skin care composition transfer test and/or the enzyme inhibitor transfer test.

E. FIGS. 2a and 2b illustrate placement location for the TEGADERM tape, shown in those figures as tape 700. Apply the tape 700 to the child's right buttock. The tape 700 is to be applied to the highest point on the child's buttock immediately adjacent to, but not in, the child's gluteal groove. A second tape 700 may be applied to measure transfer at two time increments or the effect of an additional diaper. If a second tape is used, apply the tape 700 on the left buttock using the procedure described above.

F. Change diapers according to the following protocol: 3 hour transfer time—1 diaper; 6 hour transfer time—2 diapers (change at 3 hours); 24 hour transfer times ad lib by caregiver. For 24 hour transfer times the following additional instructions are to be followed:

1. Use only water and a washcloth for cleaning the diapered area for the duration of the test. Do not use baby wipes. Avoid touching the area around the tapes with hands or any cleaning implement.
2. Do not use skin care products (lotions, ointments, creams, soap, etc.) for the duration of the test.
3. Do not bathe the subject for the duration of the test.
4. Use only the test diapers. Record the time of each diaper change.
5. Record the time of any bowel movement and clean the subject with water and a wash cloth.

G. Record the time each diaper was applied for all test diapers.

H. Recall the subject near the end of the predetermined transfer time.

I. Remove the test diaper. If the child has had a bowel movement, the study personnel should remove the tape 700 and discard it (the subject has then completed the test and data from that subject are not included in the analysis). If the subject has urinated, the tape 700 will become acceptable for analysis as described below.

J. Test facility personnel should wear surgical gloves and remove the tape 700 by grasping the edge of the tape 700 with tweezers and gently peeling the remaining portion of the tape 700 from the skin.

K. Make sure the jar is and gently peeling the remaining properly labeled for subsequent sample identification.

L. At the completion of the test collect all of the samples in the jars for analysis as described below.

1. Extraction and Analysis of Test Samples For Skin Care Composition

This method is designed for use with the preferred skin care composition, the skin care composition of Table 4. One of ordinary skill in the art will recognize what adaptations may be necessary to extract and analyze the level of other skin care compositions. In principle: 1) one of the major ingredients of the composition is extracted from the skin analog using an appropriate solvent; 2) gas chromatographic or other appropriate quantitative analytical techniques are then used to determine the level of the major ingredient in the extract; 3) amount of skin care composition is calculated per unit area based on amount of major ingredient in extract and the area of the tape.

Internal Standard/Extraction Solvent

Prepare an internal standard/extraction solvent by accurately weighing 100±2 mg of 1-hexadecanol into a small beaker. Dissolve the 1-hexadecanol in dichloromethane and transfer to a 1 liter volumetric flask. Rinse the beaker 3 more times with dichloromethane transferring each rinse portion to the volumetric flask. Fill the volumetric flask to volume and mix well. This solution will be used to deliver the internal standard and extract skin care composition from the tapes. When not being used, this container should be kept tightly capped to prevent evaporation of solvent.

Calibration Standard

Prepare a calibration standard of known concentration by accurately weighing (±0.1 mg) 10±1 mg of the stearyl alcohol into a 100 ml volumetric flask. Record the weight of stearyl alcohol used. Add the internal standard/extraction solvent to the flask and mix to dissolve. Fill to volume and mix well. When not being used, this container should be kept tightly capped to prevent evaporation of solvent. This solution will be used to determine the relative response of the stearyl alcohol to the 1-hexadecanol internal standard for calibration of the instrument.

Preparation and Calibration of the Gas Chromatograph

All equipment should be installed, operated and maintained according to manufacturer's recommendations.

Install the column and check all the gas flows with the column oven at 100° C. and the injection port and detector at operating temperatures. The GC will be operated under the following conditions:

Carrier Gas: Hydrogen (Helium may be used); flow rate 1.5 ml/min

Injection Port: 325° C.; Split vent flow 30 ml/min; Septum purge 2 ml/min; straight through liner with glass wool plug; Merlin microseal.

Injection volume: 2 $\mu$l split

FID Detector: 350° C.; set gas flows according to manufacturer suggestions. Typical gas flows are 400 ml/minute for air, 30 ml/minute for hydrogen and 30 ml/minute for the auxiliary (make up) gas.

Column Oven: 100° C. ramped at 15° C./minute to 325° C.; hold for 10 minutes

Insure that all connections are tight and leak free. Ignite the detector and allow it to stabilize. Condition the column at 325° C. for 30 minutes. Clean the syringe with dichloromethane as needed. The syringe should also be rinsed with dichloromethane several times after each injection. Make several blank runs with injections of dichloromethane to ensure that a good baseline is obtained and that no extraneous peaks are present in the chromatogram. If extraneous peaks are present or baseline is not suitable, trouble shoot and correct problem(s).

Calibrate the instrument using the calibration standard prepared previously. Consult the data system manufacturer's instructions for the proper sequence of operations. Calculations should be performed in a manner similar to that described in CALCULATIONS below in order to provide the desired result.

Sample Analysis Procedure

1) Remove the lid from the sample jar and add 10 ml of the extraction solvent/internal standard solution using the dispensing flask. Replace the cap and swirl the contents to insure that the tape 700 is not adhering to the sides of the jar and is totally submersed in solvent. Repeat for all samples.

2) Allow the samples to sit 16 hours (typically done overnight).
3) Swirl the contents of the jar to mix. Using a transfer pipette, transfer an aliquot of the sample extract to a properly labeled autosampler vial. Cap the vial. Replace jar lid and retain until analyses are complete. Repeat for all samples.
4) Place the vials in the autosampler in random order and start the analyses using the GC conditions described above. The first vial should be a dichloromethane blank. Several "check" standards should be placed (about every 20th sample) through out the run to verify correct operation.
5) At the completion of the run, check each chromatogram to insure proper analysis. If a problem is suspected, trouble shoot and correct. Reanalyze samples as needed.

Calculations

The total micrograms of stearyl alcohol in each sample extract is calculated based on the relative response of the stearyl alcohol peak to that of the 1-hexadecanol internal standard. The ratio of the peak areas is multiplied by the relative response factor (determined at time of instrument calibration) and the micrograms of internal standard in the extract to yield the total µg of stearyl alcohol in a sample.

Instrument Calibration

Determine the instrumental relative response factor for the stearyl alcohol and the internal standard based on the areas of the stearyl alcohol and 1-hexadecanol peaks in the calibration standard chromatogram.

$$\text{Response factor } (R_f) = \frac{\text{Area}_{inst}}{\text{weight}_{inst}} \times \frac{\text{weight}_{sa}}{\text{Area}_{sa}} \times 10$$

where

Area$_{inst}$=GC peak area for the internal standard
Area$_{sa}$=GC peak area for the stearyl alcohol
weight$_{inst}$=micrograms of the internal standard used to prepare internal standard/extraction solvent
weight$_{sa}$=micrograms of the stearyl alcohol used to prepare the calibration standard Sample Calculations Calculate the total micrograms of stearyl alcohol in each sample using the peak areas from the sample chromatogram in the following equation:

$$\text{Total } \mu g \, SA = \frac{\text{Area}_{sa}}{\text{Area}_{inst}} \times R_f \times \frac{\text{weight}_{inst}}{100}$$

where

Area$_{inst}$=GC peak area for the internal standard
Area$_{sa}$=GC peak area for the stearyl alcohol
weight$_{inst}$=micrograms of the internal standard used to prepare internal standard/extraction solvent Report amount of skin care composition transferred in mg/cm$^2$ where:

$$\text{Composition Transferred} = \frac{0.001 \times \mu g \text{ of stearyl alcohol}}{(\text{concentration of stearyl alcohol in composition}) \times (\text{tape area})}$$

For the method described above the concentration of stearyl alcohol in the composition is 41% and the tape patch measures 4.4 cm×4.4 cm.

$$\text{Composition Transferred} = (0.001 \times \mu g \text{ of stearyl alcohol})/$$
$$(0.41 \times 4.4 \text{ cm} \times 4.4 \text{ cm})$$
$$= 0.000126 \times \mu g \text{ of stearyl alcohol}(mg/cm^2)$$

2. Extraction and Analysis of Test Sample for Enzyme Inhibitor

This method is designed for use with the skin care composition containing a enzyme inhibitor of Table 1. One of ordinary skill in the art will recognize what adaptations may be necessary to extract and analyze the level of other enzyme inhibitors. In principle: 1) the enzyme inhibitor is extracted from the skin analog using an appropriate solvent; 2) HPLC or other quantitative analytical techniques are then used to determine the level of the inhibitor in the extract; 3) the amount of a enzyme inhibitor is calculated per unit area based on the amount of inhibitor in the extract and the area of the tape.

Preparation Of Standards

To prepare a 10 ug/mL standard solution of hexamidine, weigh 0.10 grams +/−0.02 grams of reagent grade hexamidine diisethionate and dissolve this in an HPLC mobile phase (10% glacial acetic acid and 17.5% methanol) solution. Prepare additional hexamidine standards by aliquoting the 10 ug/mL standard solution as shown in Table 2 and diluting to volume in 100 mL flasks with the HPLC mobile phase solution.

TABLE 2

Standards Preparation*

| Standard | mL hexamidine standard solution | Final Volume (mL) | Nominal Conc. (ug/mL) |
|---|---|---|---|
| 1 | 5.0 | 100 | 0.5 |
| 2 | 10.0 | 100 | 1.0 |
| 3 | 25.0 | 100 | 2.5 |
| 4 | 50.0 | 100 | 5.0 |

Sample Preparation

1. Place the transfer tape sample in a 40 mL glass vial.
2. Add 10 mL of dichloromethane to the vial using a dispensing flask, and cap the vial tightly.
3. Secure the vial in wrist-action shaker and shake for 30 minutes.
4. Remove the vial from the shaker, remove the cap of the vial and add 10 mL of the HPLC mobile phase solution to the vial. Re-cap the vial and place the vial securely in the wrist-action shaker.
5. Shake the sample for 30 minutes to dissolve the hexamidine in the aqueous phase.
6. Allow the vial/sample to sit and the layers to separate for a least 30 minutes before proceeding.
7. After the sample has separated, remove the aqueous (top layer) from the vial with a disposable syringe and filter the aqueous phase through a 0.45 micron filter into a HPLC sample vial.

Sample Analysis

1. Chromatograph the standards and the samples under the conditions described in Table 3.

TABLE 3

Chromatographic Conditions

| | |
|---|---|
| Mobile Phase Flow Rate: | 0.25 mL/mm. |
| Mobile Phase: | 10% glacial acetic acid, 17.5% methanol |
| Injection Volume: | 10 mL |
| UV Detector Wavelength: | 254 nm |
| UV Detector Sensitivity: | 1.000 AUFS |
| UV Detector Filter: | 2.0 sec |
| Run Time: | 10.0 min |

Calculations

1. Standard concentration (mg/mL):

$$S_i(mg/mL) = W(mg)/100 * (V_1/100) \quad (1)$$

W=weight of hexamidine for stock standard solution $V_1$=volume of hexamidine stock solution used to prepare the standard (Table I)

2. Calibration Curve
   A. Tabulate mg/mL of hexamidine in each standard ($S_i$) and the responses (peak areas or peak heights), $R_i$, for each of the standard solutions.
   B. Construct a calibration curve by performing a least-squares fit of equation 2 to the data.

$$R_i = mS_i + b \quad (2)$$

3. Test Samples
   A. Calculate the amount of Hexamidine ($H_1$) in sample extracts using the measured response R and the calibration equation:

$$H_1 = (R-b)/m \quad (3)$$

B. Calculate the amount of Hexamidine (H) in samples in mg according to eq. 4.

$$H = H_i * 10 \quad (4)$$

C. Divide the amount of hexamidine (H) by the tape area to determine the concentration of hexamidine per unit area of skin analog.

VIII. Specific Examples

The following are specific illustrations of (a) treating diaper topsheets with skin care compositions and (b) methods of the present invention which utilize articles comprising those topsheets. Similar approaches may be utilized to treat other components for providing treated articles for use in the present methods.

EXAMPLE 1

Preparation and Testing of an Absorbent Article Having a Topsheet Comprising a Skin Care Composition and an Enzyme Inhibitor A. Preparation of Skin Care Compositions Composition 1

A skin care composition is made by mixing the following components together: 99 parts of a melted (i.e., liquid) base composition containing 85 parts SEFA cottonate (sucrose polycottonate made by the Procter and Gamble Co., Cincinnati, Ohio) and 15 parts SEFA behenate (sucrose polybehenate made by the Procter and Gamble Co., Cincinnati, Ohio) with 1 part acetohydroxamic acid (Sigma Chemicals, St. Louis, Mo.).

Composition 2

A skin care composition is made by mixing the following components together: 99 parts of a melted (i.e., liquid) base composition containing 58 parts petrolatum (available from Witco Corp., Greenwich, Conn. as White Protopet); 41 parts stearyl alcohol (available from the Procter and Gamble Co., Cincinnati, Ohio as CO1897); and 1 part aloe extract (available from Madis Botanicals, Inc., S. Hackensack, N.J. as Veragel Lipoid in Kaydol) with 1 part tranexamic acid (Sigma Chemicals).

Composition 3

A skin care composition is prepared as in composition 2, except that triacetin (Sigma Chemicals) is employed instead of tranexamic acid.

Composition 4

A skin care composition is made by mixing the following components together: 9 parts of a melted (i.e., liquid) base composition containing 58 parts petrolatum (available from Witco Corp., Greenwich, Conn. as White Protopet); 41 parts stearyl alcohol (available from the Procter and Gamble Co., Cincinnati, Ohio as CO1897); and 1 part aloe extract (available from Madis Botanicals, Inc., S. Hackensack, N.J. as Veragel Lipoid in Kaydol) with 1 part of a heated (i.e., 60° C.) inhibitor composition containing 9 parts Tween 60 (ICI Surfactants) and 1 part hexamidine diisethionate (available from Laboratories Serobilogiques, Pulnoy, France as Elestab HP100).

B. Preparation of a Treated Article by Contact Slot Coating

A selected composition from Table 1 is placed into a heated tank operating at a temperature of 170° F. The composition is subsequently applied with a contact applicator (using, for example, a Meltex EP45 hot melt adhesive applicator head having 5 slots and operating at a temperature of 170° F.) onto the topsheet of an article in a striped pattern where the stripes run in the article's longitudinal direction. Specifically, 5 stripes are applied, each stripe measuring 0.25 in. wide (i.e., in the articles lateral direction) and 11.75 in. long at an add-on level=7.7 mg/in$^2$ (12 g/m$^2$, 1.19 mg/cm$^2$). The distance between the stripes is 0.31 in.

EXAMPLE 2

Method of Improving Skin Health

An active incontinent adult weighing 165 lbs. who constantly uses absorbent articles and who persistently has mild erythema uses an adult incontinent product analogous to the diaper of Example 1 for a period of at least about 5 days. The subject's article is changed according to the routine patterns of the user. (Typical changing patterns consist of changes every four to five hours during the day and application of a fresh article before overnight sleep.) No intervention by the user, in the form of manual application of skin protective or moisture repellent products, occurs during this period. At the end of the 5 day period, the subject is observed to have reduced or resolved erythema.

EXAMPLE 3

Method of Improving Skin Health

An infant weighing 32 lbs. exhibiting mild diaper rash and erythema is diapered for a period of at least about 5 days using the diaper of Example 1 during overnight sleep only. (That is, an untreated article is used throughout the day.) The infant's diaper is changed according to the routine patterns of the caregiver. No intervention by the caregiver, in the form of manual application of skin protective or moisture repellent products, occurs during this period. At the end of the 5 day period, the subject is observed to have reduced or resolved rash and erythema.

EXAMPLE 4

Method of Maintaining Skin Health

An infant weighing 25 lbs. exhibiting no diaper rash or erythema is diagnosed with otitis media and is prescribed a course of systemic antibiotics. Based on experience with conventional (untreated) diapers, the caregiver expects that the infant will develop erythema and/or diaper rash resulting from loose stools. As a result, diapers such as that described in Example 1 are used continuously throughout the period of administration of the antibiotic. No intervention by the caregiver, in the form of manual application of skin protective or moisture repellent products, occurs during this period. Throughout the period of antibiotic administration, the subject exhibits no erythema or diaper rash.

The disclosures of all patents, patent applications (and any patents which issue thereon, as well as any corresponding published foreign patent applications), and publications mentioned throughout this description are hereby incorporated by reference herein. It is expressly not admitted, however, that any of the document incorporated by reference herein teach or disclose the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a skin care composition disposed on at least a portion of the article, the skin care composition is solid or semi-solid at 20° C. and comprises (i) from about 0.001% to about 50% of an enzyme inhibitor, (ii) from about 5% to about 95% of an emollient having a plastic or fluid consistency at 20° C., and (iii) from about 5% to about 95% of an agent capable of immobilizing the emollient in the article, wherein the immobilizing agent has a melting point of at least about 35° C. and the enzyme inhibitor has an $IC_{50}$ of about 50 $\mu$M or less, as measured by a General Fecal Enzyme Method.

2. The article of claim 1, wherein the enzyme inhibitor is selected from the group consisting of a protease inhibitor, a lipase inhibitor, an elastase inhibitor, a urease inhibitor, an amylase inhibitor, and combinations thereof.

3. The article of claim 1, wherein the portion of the article is selected from the group consisting of a backsheet, a topsheet, an absorbent core, a leg cuff, a side panel, a waist region, a fastener, a secondary layer intermediate the absorbent core and the topsheet or the backsheet, a nanophase structural element, a bowel movement pocket, an insertable element inserted into the absorbent article for use during wear of the article, and combinations thereof.

4. The article of claim 3, wherein the portion of the article is a wearer-contacting surface.

5. The article of claim 4, wherein the wearer-contacting surface is the topsheet.

6. The article of claim 5, wherein the skin care composition comprising the enzyme inhibitor is applied to the topsheet such that one or more regions of the topsheet are not treated with the skin care composition.

7. The article of claim 6, wherein the skin care composition comprising the enzyme inhibitor is applied to the topsheet in the form of a plurality of stripes that are separated by a plurality of stripes having no skin care composition.

8. The article of claim 1, wherein the skin care composition is applied to the topsheet at a level in the range of about 0.05 mg/in$^2$ (0.0078 mg/cm$^2$) to about 80 mg/in$^2$ (12 mg/cm$^2$).

9. The article of claim 1, wherein at least about 0.01 mg/in$^2$ (0.0016 mg/cm$^2$) of the skin care composition containing the enzyme inhibitor is transferred to the wearer's skin during use of the article treated with the skin care composition.

10. The article of claim 1, wherein the skin care composition comprises a petroleum-based emollient selected from the group consisting of mineral oil, petrolatum, and mixtures thereof.

11. The article of claim 1, wherein the skin care composition further comprises a member selected from the group consisting of fatty acid ester type emollients; alkyl ethoxylate type emollients; fatty acid ester ethoxylates emollients; fatty alcohol type emollients; polysiloxane-type emollients; sucrose ester fatty acids; polyethylene glycol and derivatives thereof; sorbitol and derivatives thereof; trihydroxystearin and derivatives thereof; humectants; dimethicone, propylene glycol and derivatives thereof; glycerine and derivatives thereof; triethylene glycol and derivatives thereof; spermaceti or other waxes; fatty acids; fatty alcohol ethers; propoxylated fatty alcohols; fatty esters of polyhydroxy alcohols; lanolin and its derivatives; kaolin and its derivatives; alantoin; aluminum hydroxide gel; calamine; cocoa butter; cod liver oil; kaolin; lanolin; mineral oil; shark liver oil; white petrolatum talc; topical starch; zinc acetate; zinc carbonate; zinc oxide; live yeast cell derivatives; aldioxa; aluminum acetate; microporous cellulose; cholecalciferol; colloidal oatmeal; cysteine hydrochloride; dexpanthanol; Peruvian balsam oil; protein hydrolysates; racemic methionine; sodium bicarbonate; Vitamin A, $D_3$, E, $B_5$ and E acetate; and mixtures thereof.

12. The article of claim 1 in which the enzyme inhibitor is selected from the group consisting of: soybean trypsin inhibitor and other plant-derived trypsin inhibitors; Bowman-Birk inhibitor; pancreatic trypsin inhibitor; ovomucoids; chymostatin; aprotinin; leupeptin and its analogs; bestatin and its analogs; antipain; antithrombin III; hirudin, cystatin; $\alpha_2$-macroglobulin; $\alpha_1$-antitrypsin; pepstatin and its analogs; TLCK; TPCK; tranexamic acid and its salts; glycyrrhizic acid and its salts; stearylglycyrrhetinate; 18-$\beta$-glycyrrhetinic acid and its salts; colloidal oat extracts; elhibin; 4-(2-aminoethyl)-benzenesulfonylfluoride HCl; quercetin; phytic acid and its salts; ethylenediamine tetraacetic acid (EDTA) and its salts; hexamidine and its salts; pentamideine and its salts; benzamidine and its salts and derivatives; p-aminobenzamidine and its salts and derivatives; guanidinobenzoic acid and its salts and derivatives, including its polymeric derivatives; alkyl hydroxamic acids and corresponding salts and derivatives; phosphoramidate and its derivatives; water soluble salts of metals; zinc salts of both saturated and unsaturated monocarboxylic acids; glycerol trimesters of fatty acids, such as triacetin; block copolymers of propylene oxide and ethylene oxide; chlorhexidine; cholestyramine; acarbose; voglibose; miglitol; emiglitate; camiglibose; pradimicin Q; salbostatin; tendamistat; trestatins; inhibitors derived from plants, especially those from wheat, rice, maize, barley and other cereal grains, beans, and seaweed; tetrahydrolipstatin; lipstatin; valilactone; esterastin; ebelactone A and B; 1,6-di(O-(carbamoyl)cyclohexanone oxime)hexane; and mixtures thereof.

13. An absorbent article containing the skin care composition that comprises an enzyme inhibitor, wherein the enzyme inhibitor has an $IC_{50}$ of about 50 $\mu$M or less, as measured by a General Fecal Enzyme Method, and the skin care composition comprising the enzyme inhibitor is at least partially transferred from the article to the skin of a wearer of the article as a result of normal contact, wearer motion, and/or body heat.

14. The article of claim 13, wherein the skin care composition is solid or semi-solid at 20° C.

15. The article of claim 13, wherein the skin care composition further comprises about 5% to about 95% of an emollient having a plastic or fluid consistency at 20° C.

16. The article of claim 15, further comprising about 5% to about 95% of an agent capable of immobilizing the emollient in the article and having a melting point of at least 35° C.

17. The article of claim 13, wherein the skin care composition comprises from about 0.001% to about 50% of the enzyme inhibitor.

18. The article of claim 13, wherein the enzyme inhibitor is selected from the group consisting of a protease inhibitor, a lipase inhibitor, an elastase inhibitor, a urease inhibitor, an amylase inhibitor, and combinations thereof.

19. A method for reducing the enzymatic activity of a fecal enzyme on a portion of the skin of a wearer of an absorbent article, comprising the steps of (i) providing an absorbent article, at least a portion of which comprises a skin care composition that comprises an enzyme inhibitor, the enzyme inhibitor has an $IC_{50}$ of about 50 $\mu$M or less, as measured by a General Fecal Enzyme Method, and (ii) transferring a portion of the skin care composition to the skin of the wearer during wear of the article.

20. The method of claim 19, wherein the portion of the article is a wearer-contacting surface.

21. The method of claim 19, wherein the wearer-contacting surface is a liquid pervious topsheet.

22. The method of claim 19, wherein the skin care composition is solid or semi-solid at 20° C.

23. The method of claim 22, wherein the skin care composition further comprises (i) about 5% to about 95% of an emollient having a plastic or fluid consistency at 20° C., and (ii) about 5% to about 95% of an agent capable of immobilizing the emollient on an outer surface of the topsheet, the immobilizing agent having a melting point of at least about 35° C.

24. The method of claim 19, wherein the skin care composition is applied to the topsheet at a level in the range of about 0.05 mg/in$^2$ (0.0078 mg/cm$^2$) to about 80 mg/in$^2$ (12 mg/cm$^2$).

\* \* \* \* \*

UNITED STATES PATENT AND TRADEMARK OFFICE
CERTIFICATE OF CORRECTION

PATENT NO. : 6,703,536 B2
APPLICATION NO. : 10/323386
DATED : March 9, 2006
INVENTOR(S) : Roe et al.

It is certified that error appears in the above-identified patent and that said Letters Patent is hereby corrected as shown below:

Column 1

Line 10, please delete "now abandoned".

Column 5

Line 5, please delete "AM" and insert -- µM--.

Column 6

Line 42, please delete "NIe" and insert--Nle--.

Column 12

Line 2, please delete "spuniace" and insert--spunlace--.

Column 17

Line 59, please delete entire equation and replace it with the following:

$$IC_{50} = [I]/[(v/v_i)-1],$$

Column 21

Please delete "TABLE 1 – continued" starting at line 1 through the line before "**TLCK = …"

UNITED STATES PATENT AND TRADEMARK OFFICE
CERTIFICATE OF CORRECTION

PATENT NO. : 6,703,536 B2
APPLICATION NO. : 10/323386
DATED : March 9, 2006
INVENTOR(S) : Roe et al.

It is certified that error appears in the above-identified patent and that said Letters Patent is hereby corrected as shown below:

Column 23

Line 22, please delete "a-Amylase" and insert --α-Amylase--.

Column 32

Line 11, please delete "$C_5$-$C_3$," and insert --$C_5$-$C_{31}$,--.

Line 52, please delete "$C_1$-$C_{17}$" and insert --$C_{11}$-$C_{17}$--.

Column 33

Line 18, please delete "camauba" and insert --carnauba--.

Column 45

Line 5, please delete "m m" and insert --min.--.

Signed and Sealed this

Twenty-ninth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,703,536 B2
APPLICATION NO. : 10/323386
DATED : March 9, 2004
INVENTOR(S) : Roe et al.

It is certified that error appears in the above-identified patent and that said Letters Patent is hereby corrected as shown below:

Column 1

Line 10, please delete "now abandoned".

Column 5

Line 5, please delete "AM and insert -- $\mu M$--.

Column 6

Line 42, please delete "NIe" and insert--Nle--.

Column 12

Line 2, please delete "spuniace" and insert--spunlace--.

Column 17

Line 59, please delete entire eqauation and replace it with the following:

--$IC_{50} = [I]/[(v/v_i)-1]$,--

Column 21

Please delete "TABLE 1 – continued" starting at line 1 through the line before "**TLCK = ..."

Column 23

Line 22, please delete "a-Amylase" and insert --α-Amylase--.

UNITED STATES PATENT AND TRADEMARK OFFICE
CERTIFICATE OF CORRECTION

PATENT NO. : 6,703,536 B2
APPLICATION NO. : 10/323386
DATED : March 9, 2004
INVENTOR(S) : Roe et al.

It is certified that error appears in the above-identified patent and that said Letters Patent is hereby corrected as shown below:

Column 32

Line 11, please delete "$C_5$-$C_3$," and insert --$C_5$-$C_{31}$,--.

Line 52, please delete "$C_1$-$C_{17}$" and insert --$C_{11}$-$C_{17}$--.

Column 33

Line 18, please delete "camauba" and insert --carnauba--.

Column 45

Line 5, please delete "m m" and insert --min.--.

This certificate supersedes Certificate of Correction issued August 29, 2006.

Signed and Sealed this

Tenth Day of October, 2006

JON W. DUDAS
*Director of the United States Patent and Trademark Office*